(12) United States Patent
McNair

(10) Patent No.: US 11,488,699 B1
(45) Date of Patent: Nov. 1, 2022

(54) MICROBIOTA ACTIVITY SENSOR AND DECISION SUPPORT TOOL

(71) Applicant: CERNER INNOVATION, INC., Kansas City, KS (US)

(72) Inventor: Douglas S. McNair, Seattle, WA (US)

(73) Assignee: CERNER INNOVATION, INC., North Kansas City, MO (US)

( * ) Notice: Subject to any disclaimer, the term of this patent is extended or adjusted under 35 U.S.C. 154(b) by 450 days.

(21) Appl. No.: 16/707,786

(22) Filed: Dec. 9, 2019

Related U.S. Application Data

(60) Provisional application No. 62/777,201, filed on Dec. 9, 2018.

(51) Int. Cl.
| | | |
|---|---|---|
| *G16H 20/10* | (2018.01) | |
| *G16H 50/20* | (2018.01) | |
| *G06F 17/17* | (2006.01) | |
| *G06F 17/18* | (2006.01) | |

(52) U.S. Cl.
CPC ............. *G16H 20/10* (2018.01); *G16H 50/20* (2018.01); *G06F 17/17* (2013.01); *G06F 17/18* (2013.01)

(58) Field of Classification Search
CPC ........ G16H 20/10; G16H 50/20; G06F 17/17; G06F 17/18
See application file for complete search history.

(56) References Cited

U.S. PATENT DOCUMENTS

| | | | |
|---|---|---|---|
| 8,478,544 | B2 | 7/2013 | Colwell et al. |
| 9,663,831 | B2 | 5/2017 | Apte et al. |

(Continued)

FOREIGN PATENT DOCUMENTS

| | | |
|---|---|---|
| EP | 3262215 A1 | 1/2018 |
| WO | 2011/053831 A1 | 5/2011 |

(Continued)

OTHER PUBLICATIONS

Engelhart et al., "Disease Associations with Isolated Elevations of each of the four IgG Subclasses", Seminars in Arthritis and Rheumatism, vol. 47, No. 2, 2017, pp. 276-280.

(Continued)

*Primary Examiner* — Kabir A Timory
(74) *Attorney, Agent, or Firm* — Shook, Hardy & Bacon L.L.P.

(57) ABSTRACT

An improved decision support tool is provided for detecting, diagnosing, or treating human patient based on detected changes or trends in microbiota-related activity of the patient. The decision support tool determine a longitudinal pattern of relative abundances or diversity levels of microbiota, and subsequently determine the occurrence of alternations or trends, which may indicate or be related to meaningful clinical events, such as a change in condition for the patient. In one embodiment, a joint determination of statistical significance of change and trend is first detected and then utilized to determine an occurrence of clinically meaningful microbiota activity in a patient. The decision support tool may further initiate an intervening action based on a detected change or trend, such as generating an electronic notification, modifying a treatment program, providing a recommendation, automatically allocating health care resources to the patient, or automatically scheduling a consultation with a caregiver.

20 Claims, 18 Drawing Sheets

(56) References Cited

U.S. PATENT DOCUMENTS

| | | |
|---|---|---|
| 9,703,929 B2 | 7/2017 | Apte et al. |
| 9,719,144 B2 | 8/2017 | Krajmalnik-Brown et al. |
| 9,739,786 B2 | 8/2017 | Westin et al. |
| 9,758,839 B2 | 9/2017 | Apte et al. |
| 9,760,676 B2 | 9/2017 | Apte et al. |
| 10,668,118 B2 * | 6/2020 | Lynch ................ A61K 39/0008 |
| 10,954,571 B2 * | 3/2021 | Mougeot .......... G01N 33/56911 |
| 2016/0120915 A1 | 5/2016 | Blaser et al. |
| 2016/0263166 A1 | 9/2016 | Elinav et al. |
| 2017/0286620 A1 | 10/2017 | Apte et al. |
| 2018/0010164 A1 | 1/2018 | Taneja |
| 2020/0399673 A1 | 12/2020 | Kashyap |

FOREIGN PATENT DOCUMENTS

| | | |
|---|---|---|
| WO | 2013/012332 A1 | 1/2013 |
| WO | 2014/188378 A1 | 11/2014 |

OTHER PUBLICATIONS

Hamed, Khaled H., "Trend Detection in Hydrologic Data: The Mann-Kendall Trend Test Under the Scaling Hypothesis", Journal of Hydrology, vol. 349, No. 3-4, 2008, pp. 350-363.

Hussain et al., "Significantly Increased IgG2 Subclass Antibody Levels to Blastocystis Hominis in Patients with Irritable Bowel Syndrome", The American Society of Tropical Medicine and Hygiene, vol. 56, No. 3, Mar. 1997, pp. 301-306.

Floch et al., "The Microbiota in Gastrointestinal Pathophysiology: Implications for Human Health, Prebiotics, Probiotics, and Dysbiosis", Academic Press, 2016, 442 pages.

Izard et al., "Metagenomics for Microbiology", Academic Press, 2014, 188 pages.

Pre interview First Office Action received for U.S. Appl. No. 16/717,801, dated Aug. 4, 2022, 4 pages.

* cited by examiner

| 1 | TAX_NAME | TAX_RANK | COUNT | COUNT_NOR | TAXON | PARENT |
|---|---|---|---|---|---|---|
| 2 | ROOT | ROOT | 71114 | 1000000 | 1 | 0 |
| 3 | BACTERIA | SUPERKING | 71114 | 1000000 | 2 | 131567 |
| 4 | BACTEROIDACEAE | FAMILY | 16605 | 233498 | 815 | 171549 |
| 5 | BACTEROIDES | GENUS | 16600 | 233428 | 816 | 815 |
| 6 | BACTEROIDES THETAIOTAOMICRON | SPECIES | 11 | 154 | 818 | 816 |
| 7 | BACTEROIDES UNIFORMIS | SPECIES | 91 | 1279 | 820 | 816 |
| 8 | BACTEROIDES VULGATUS | SPECIES | 11493 | 161613 | 821 | 816 |
| 9 | PARABACTEROIDES DISTASONIS | SPECIES | 1146 | 16114 | 823 | 375288 |
| 10 | ROSEBURIA | GENUS | 5112 | 71884 | 841 | 186803 |
| 11 | FAECALIBACTERIUM PRAUSNITZII | SPECIES | 4617 | 64923 | 853 | 216851 |
| 12 | DESULFOVIBRIO | GENUS | 2 | 28 | 872 | 194924 |
| 13 | DESULFOVIBRIO SP. | SPECIES | 2 | 28 | 885 | 872 |
| 14 | HERBASPIRILLUM | GENUS | 10 | 140 | 963 | 75682 |
| 15 | HERBASPIRILLUM SEROPEDICAE | SPECIES | 10 | 140 | 964 | 963 |
| 16 | BACTEROIDETES | PHYLUM | 21020 | 295581 | 976 | 68336 |
| 17 | PROTEOBACTERIA | PHYLUM | 2467 | 34690 | 1224 | 2 |
| 18 | FIRMICUTES | PHYLUM | 45069 | 633757 | 1239 | 2 |
| 19 | SARCINA | GENUS | 781 | 10982 | 1266 | 31979 |
| 20 | STREPTOCOCCACEAE | FAMILY | 957 | 13457 | 1300 | 186826 |
| 21 | STREPTOCOCCUS | GENUS | 930 | 13077 | 1301 | 1300 |
| 22 | STREPTOCOCCUS THERMOPHILUS | SPECIES | 877 | 12332 | 1308 | 1301 |
| 23 | LACTOCOCCUS | GENUS | 5 | 70 | 1357 | 1300 |
| 24 | BACILLALES | ORDER | 2 | 28 | 1385 | 91061 |
| 25 | CLOSTRIDIUM | GENUS | 658 | 9252 | 1485 | 31979 |
| 26 | LACTOBACILLUS | GENUS | 38 | 534 | 1578 | 33958 |
| 27 | LACTOBACILLUS DELBRUECKII | SPECIES | 9 | 126 | 1584 | 1578 |
| 28 | CORYNEBACTERIACEAE | FAMILY | 3 | 42 | 1653 | 85007 |
| 29 | BIFIDOBACTERIUM | GENUS | 3 | 42 | 1678 | 31953 |

.
.

~200 TO ~500 MORE ROWS IN TABLE

*FIG. 6.*

```
###########################################################################

#   Microbiota serial abundances rarefaction, phylogenetic distance calculation,
#   time-oriented MANOVA, Hurst-Kolmogorov trend analysis

##################################################################### library(permute)
library(lattice)
library(vegan)
library(ape)
library(GUniFrac)
library(qiimer)
# source("https://bioconductor.org/biocLite.R")
# biocLite("phyloseq")
library(phyloseq)

library(SparseM)
library(MatrixModels)
library(coda)
library(mcmc)
library(quantreg)
library(MCMCpack)
library(gtools)
library(HKprocess)

# define distance-based multivariate analysis of variance MANOVA function
dbmanova <- function (formula, data = NULL, permutations = 999, method = "bray",
    strata = NULL, contr.unordered = "contr.sum", contr.ordered = "contr.poly",
    parallel = getOption("mc.cores"), ...)
{
    EPS <- sqrt(.Machine$double.eps)
    TOL <- 1e-07
    Terms <- terms(formula, data = data)
    lhs <- formula[[2]]
    lhs <- eval(lhs, data, parent.frame())
    formula[[2]] <- NULL
    rhs.frame <- model.frame(formula, data, drop.unused.levels = TRUE)
    op.c <- options()$contrasts
    options(contrasts = c(contr.unordered, contr.ordered))
    rhs <- model.matrix(formula, rhs.frame)
    options(contrasts = op.c)
    grps <- attr(rhs, "assign")
    qrhs <- qr(rhs)
    rhs <- rhs[, qrhs$pivot, drop = FALSE]
    rhs <- rhs[, 1:qrhs$rank, drop = FALSE]
    grps <- grps[qrhs$pivot][1:qrhs$rank]
    u.grps <- unique(grps)
    nterms <- length(u.grps) - 1
```

⋮

CONTINUES IN FIG. 9B

*FIG. 9A.*

CONTINUES FROM FIG. 9A

⋅
⋅

```
if (nterms < 1)
   stop("right-hand-side of formula has no usable terms")
H.s <- lapply(2:length(u.grps), function(j) {
   Xj <- rhs[, grps %in% u.grps[1:j]]
   qrX <- qr(Xj, tol = TOL)
   Q <- qr.Q(qrX)
   tcrossprod(Q[, 1:qrX$rank])
})
if (inherits(lhs, "dist")) {
   if (any(lhs < -TOL))
      stop("dissimilarities must be non-negative")
   dmat <- as.matrix(lhs^2)
}
else if ((is.matrix(lhs) || is.data.frame(lhs)) && isSymmetric(unname(as.matrix(lhs)))) {
   dmat <- as.matrix(lhs^2)
   lhs <- as.dist(lhs)
}
else {
   dist.lhs <- as.matrix(vegdist(lhs, method = method, ...))
   dmat <- dist.lhs^2
}
n <- nrow(dmat)
G <- -sweep(dmat, 1, rowMeans(dmat))/2
SS.Exp.comb <- sapply(H.s, function(hat) sum(G * t(hat)))
SS.Exp.each <- c(SS.Exp.comb - c(0, SS.Exp.comb[-nterms]))
H.snterm <- H.s[[nterms]]
tIH.snterm <- t(diag(n) - H.snterm)
if (length(H.s) > 1)
   for (i in length(H.s):2) H.s[[i]] <- H.s[[i]] - H.s[[i -
      1]]
SS.Res <- sum(G * tIH.snterm)
df.Exp <- sapply(u.grps[-1], function(i) sum(grps == i))
df.Res <- n - qrhs$rank
if (inherits(lhs, "dist")) {
   beta.sites <- qr.coef(qrhs, as.matrix(lhs))
   beta.spp <- NULL
}
else {
   beta.sites <- qr.coef(qrhs, dist.lhs)
   beta.spp <- qr.coef(qrhs, as.matrix(lhs))
}
colnames(beta.spp) <- colnames(lhs)
colnames(beta.sites) <- rownames(lhs)
F.Mod <- (SS.Exp.each/df.Exp)/(SS.Res/df.Res)
f.test <- function(tH, G, df.Exp, df.Res, tIH.snterm) {
   (sum(G * tH)/df.Exp)/(sum(G * tIH.snterm)/df.Res)
}
SS.perms <- function(H, G, I) {
   c(SS.Exp.p = sum(G * t(H)), S.Res.p = sum(G * t(I - H)))
}
```

CONTINUES IN FIG. 9C

CONTINUES FROM FIG. 9B

```
    p <- getPermuteMatrix(permutations, n, strata = strata)
    permutations <- nrow(p)
    if (permutations) {
      tH.s <- lapply(H.s, t)
      if (is.null(parallel))
         parallel <- 1
      hasClus <- inherits(parallel, "cluster")
      isParal <- hasClus || parallel > 1
      isMulticore <- .Platform$OS.type == "unix" && !hasClus
      if (isParal && !isMulticore && !hasClus) {
         parallel <- makeCluster(parallel)
      }
      if (isParal) {
         if (isMulticore) {
            f.perms <- sapply(1:nterms, function(i) unlist(mclapply(1:permutations,
               function(j) f.test(tH.s[[i]], G[p[j, ], p[j,
               ]], df.Exp[i], df.Res, tIH.snterm), mc.cores = parallel)))
         }
         else {
            f.perms <- sapply(1:nterms, function(i) parSapply(parallel,
               1:permutations, function(j) f.test(tH.s[[i]],
               G[p[j, ], p[j, ]], df.Exp[i], df.Res, tIH.snterm)))
         }
      }
      else {
         f.perms <- sapply(1:nterms, function(i) sapply(1:permutations,
            function(j) f.test(tH.s[[i]], G[p[j, ], p[j,
            ]], df.Exp[i], df.Res, tIH.snterm)))
      }
      if (isParal && !isMulticore && !hasClus)
         stopCluster(parallel)
      P <- (rowSums(t(f.perms) >= F.Mod - EPS) + 1)/(permutations +
         1)
    }
    else {
      f.perms <- P <- rep(NA, nterms)
    }
    SumsOfSqs = c(SS.Exp.each, SS.Res, sum(SS.Exp.each) + SS.Res)
    tab <- data.frame(Df = c(df.Exp, df.Res, n - 1), SumsOfSqs = SumsOfSqs,
      MeanSqs = c(SS.Exp.each/df.Exp, SS.Res/df.Res, NA), F.Model = c(F.Mod,
         NA, NA), R2 = SumsOfSqs/SumsOfSqs[length(SumsOfSqs)],
      P = c(P, NA, NA))
    rownames(tab) <- c(attr(attr(rhs.frame, "terms"), "term.labels")[u.grps],
      "Residuals", "Total")
    colnames(tab)[ncol(tab)] <- "Pr(>F)"
    attr(tab, "heading") <- c(howHead(attr(p, "control")), "Terms added sequentially (first to last)\n")
    class(tab) <- c("anova", class(tab))
    out <- list(aov.tab = tab, call = match.call(), coefficients = beta.spp,
      coef.sites = beta.sites, f.perms = f.perms, model.matrix = rhs,
      terms = Terms)
    out
}
```

*FIG. 9C.*

CONTINUES IN FIG. 9D

CONTINUES FROM FIG. 9C

.
.

```
# prepare to load serial Crohn's disease fecal microbiome taxa and abundances time series data (example with
10 specimens pre- and post-treatment)
prefix <- "c:/0_cerdsm/IP/microbiome_stability/dsm_ubiome_export_"
fil <- c("87450","89682","89060","91060","91089","91931","91975","93819","93909","102504")
#        basal ............................  post-treatment .......................
suffix <- ".csv"
len.ts <- length(fil)
ts.tax <- rep(0,len.ts)
ts.div <- rep(0,len.ts)

# load the time series microbiome data and perform rank-abundance distribution fittting quality check
for (i in 1:len){
  taxa.ab <- paste0(prefix, fil[i], suffix)
  dat <- read.csv(file=taxa.ab, header=TRUE, colClasses=c("character","factor",rep("integer",4)))
  # tax_name, tax_rank, count, count_norm, taxon, parent
  #
  dat1 <- dat[which(dat[,2] == "genus"),]
  len1 <- length(dat1[,1])
  dat1 <- dat1[-which(dat1[,4] < 500),] # truncate taxons having low counts
  OTUvars <- dat1[,1]
  dat2 <- matrix(as.integer(dat1[,4]), nrow=1)
  colnames(dat2) <- OTUvars
  dat2 <- sort(dat2[1,], decreasing=TRUE)
  OTUvars <- attr(dat2, "names")
  dat2 <- matrix(dat2, nrow=1)
  colnames(dat2) <- OTUvars
  fecal.otu.tab <- dat2
  # perform rank abundance distribution-fitting (preferably log-normal distribution)
  rad2 <- rad.lognormal(dat2, link=gaussian)
  # retrieve numerical-index phylogenetic tree and distance matrix
  fecal.tree <- dat1[,5]  # class 'phylo' tree constructed using UPGMA on the K80 distance matrix of the OTUs
  # retrieve meta data for treatment epochs in time series
  rx <- dat1[,6]       # pre-infliximab, infliximab
  # rarefaction of total abundance counts to a standard 10,000 16S DNA sequence reads
  fecal.otu.tab.rff <- Rarefy(fecal.otu.tab, depth=10000)$otu.tab.rff
  # calculate generalized variance-adjusted UniFrac diversity metric
  unifracs <- GUniFrac(fecal.otu.tab.rff, throat.tree, alpha=c(0, 0.5, 1))$unifracs
  dv <- unifracs[, , "d_VAW"]  # variance-adjusted UniFrac
  ts.div[i] <- dv
  # retrieve rarefacted abundance of F. prausnitzii in this sample
  ts.tax[i] <- fecal.otu.tab.rff[which(dat1[,5] == 853),2]
}
```

.
.

CONTINUES IN FIG. 9E

*FIG. 9D.*

CONTINUES FROM FIG. 9D

.
.

```
# perform distance-based multivariate analysis of variance to determine presence of change in treatment epochs
div.MANOVA.result <- dbmanova(as.dist(ts.div) ~ rx)
div.MANOVA.result
# Number of permutations: 999

#          Df SumsOfSqs  MeanSqs F.Model     R2  Pr(>F)
# rx        1   0.09269 0.092693  1.8841 0.03146   0.089
# Residuals 58  2.85342 0.049197         0.96854
Total     59  2.94612          1.00000 check model predictions by treatment group
which(rx == "pre-infliximab")
# [1] 1 2 3 4
which(result$model.matrix[,2] == -1)
# [1] 1 2 3 4

# conclude that significant difference at p < 0.1 exists and correctly identifies "pre-infliximab" vs. "infliximab-
treated" specimens
# as having different UniFrac phylogenetic diversity, consistent with effectiveness of the anti-TNF infliximab
treatment for Crohn's Disease determine presence of change/trend in F. prausnitzii abundance time series by Hurst-Kolmogorov Bayesian
methods
taxon.trend <- mleHK(ts.tax)
tax.H.result <- taxon.trend[3]
tax.H.result
#   0.8921871311

# H_estimate > 0.75 therefore, conclude significant trend exists, either as shift or drift
tax.HK.MK.result <- MannKendallLTP(ts.tax)
tax.HK.MK.result[[3]][2]
# 2_sided_pvalue
#   0.0004454069
Mann-Kendall p-value < 0.05 therefore, conclude significant trend exists, either as shift or drift combine evidence from diversity-oriented MANOVA and taxa-oriented Hurst-Kolmogorov trend analysis to
produce interpretation and emit advice
interp <- NULL
if (div.MANOVA.result && tax.HK.MK.result) interp <- "Statistically significant trend in microbiota diversity and
condition-related taxa exist."
# emit interp advice to clinician electronically

```

*FIG. 9E.*

```
fecal.otu.tab <- dat2
# perform rank abundance distribution-fitting (preferably log-normal distribution)
rad2 <- rad.lognormal(dat2, link=gaussian)
# retrieve numerical-index phylogenetic tree and distance matrix
fecal.tree <- dat1[,5]   # class 'phylo' tree constructed using UPGMA on the K80 distance matrix
# retrieve meta data for treatment epochs in time series
rx <- dat1[,6]           # pre-infliximab, infliximab
# rarefaction of total abundance counts to a standard 10,000 16S DNA sequence reads
fecal.otu.tab.rff <- Rarefy(fecal.otu.tab, depth=10000)$otu.tab.rff
# calculate generalized variance-adjusted UniFrac diversity metric
unifracs <- GUniFrac(fecal.otu.tab.rff, throat.tree, alpha=c(0, 0.5, 1))$unifracs
dv <- unifracs[, , "d_VAW"]   # variance-adjusted UniFrac
ts.div[i] <- dv
# retrieve rarefacted abundance of F. prausnitzii in this sample
ts.tax[i] <- fecal.otu.tab.rff[which(dat1[,5] == 853),2]
```

FIG. 10A.

```
# perform distance-based multivariate analysis of variance
result <- dbmanova(as.dist(dv) ~ rx)
result
# Number of permutations: 999

#           Df SumsOfSqs  MeanSqs F.Model      R2  Pr(>F)
# rx         1   0.09269 0.092693  1.8841 0.03146   0.089
# Residuals 58   2.85342 0.049197         0.96854
Total     59   2.94612                  1.00000 check model predictions by treatment group
which(rx == "pre-infliximab")
# [1] 1 2 3 4
which(result$model.matrix[,2] == -1)
# [1] 1 2 3 4

# conclude that significant difference at p < 0.1 exists
```

FIG. 10B.

```
# determine presence of change/trend in F. prausnitzii abundance time series
taxon.trend <- mleHK(ts.tax)
tax.H.result <- taxon.trend[3]
tax.H.result
#   0.8921871311

# H_estimate > 0.75 therefore, conclude significant trend exists
tax.HK.MK.result <- MannKendallLTP(ts.tax)
tax.HK.MK.result[[3]][2]
# 2_sided_pvalue
#   0.0004454069
Mann-Kendall p-value < 0.05 therefore, conclude significant trend exists combine evidence from diversity-oriented MANOVA and taxa-oriented Hurst-Ko
interp <- NULL
if (div.MANOVA.result && tax.HK.MK.result) interp <- "Statistically signif"
# emit interp advice to clinician electronically

```

FIG. 10C.

MICROBIOTA ACTIVITY SENSOR AND DECISION SUPPORT TOOL

BACKGROUND

The human body is host to a complex and abundant aggregation of microbes, collectively referred to as the microbiota. Anatomical sites that are the subject of measurements of microbiota include gut, skin, genitals, oropharynx, and respiratory tract. Microbiota in body fluids such as blood, urine, and sputum are also routinely measured. The relevance of such measurements to medical diagnostics and therapeutics is diverse. By way of example, the gut microbiota has physiological functions associated with nutrition, the immune system, and defense of the host. The intestinal microbiota plays a number of important roles in mammalian health, including gut development, extraction of energy from food, protection against pathogens, and development, maturation, and responsiveness of the immune system. Alterations in the composition of the intestinal bacterial communities have been implicated in obesity, inflammatory bowel disease, diabetes, and a variety of disease states. However, to date, the conventional technology and approaches to healthcare decision support have not understood or effectively utilized the range of gut microbiota compositional states during health in efforts to define and characterize prognosis, progression of illness, and treatment effectiveness.

SUMMARY

This summary is provided to introduce a selection of concepts in a simplified form that are further described below in the detailed description. This summary is not intended to identify key features or essential features of the claimed subject matter, nor is it intended to be used in isolation as an aid in determining the scope of the claimed subject matter.

Technologies described herein provide an improved decision support tool for treating or modifying care provided to human patients based on detected changes or trends in microbiota, and in particular based on statistically significant changes or temporal patterns. At a high level, embodiments of the technology described herein may (1) determine microbiota diversity, relative abundances of microbial taxa, or trends in the relative abundances in specimens collected from a human patient, (2) automatically ascertain whether changes in temporal patterns of microbiota diversity or relative levels of taxa are statistically significant and therefore clinically actionable, and (3) if so, automatically initiate an intervening action, such as issuing a notification or alert, scheduling healthcare resources, or generating or modifying a care plan for the patient, or generating decision support recommendations, which may include statistically robust quantitative interpretations of the patterns or pattern changes. In some embodiments, one or more longitudinal patterns of operational taxonomic units' (OTUs') relative abundances or diversity are determined and monitored for statistically significant alterations or trends in the longitudinal pattern(s). Where such alterations or trends are detected, an intervening action is initiated. In this way, embodiment described herein provide improved clinical decision support tools for preventive, diagnostic, and therapeutic applications of medicine. In particular, emerging health conditions, which may include deterioration, sickness, health risks, disease, or altercation, for example, may be identified sooner or in a less invasive manner Thus, by employing the techniques described herein, embodiments can overcome the deficiencies that are associated with the conventional industry practice.

In some embodiments, prior to determining microbiota diversity, a rarefaction method is utilized in order to compare microbiomes on an equal basis. Additionally, some embodiments entail jointly determining both the relation of microbiota diversity to a patient treatment and the relation of disease-related taxa abundances to time under different treatment regimens. Accordingly, embodiments provide for new and improved decision support systems and/or methods that are unknown within the industry, thereby providing enhanced decision support systems and methods. The decision support systems are said to be enhanced since they achieve determinations and results that have not been possible using prior technological solutions. That is, prior technological solutions were incapable of providing the unique determinations that are achieved by employing the techniques and logical structures described herein.

BRIEF DESCRIPTION OF THE DRAWINGS

The present invention is described in detail below with reference to the attached drawing figures, wherein:

FIG. 6 depicts example results from 16S rRNA pyrosequencing, according to the process of FIG. 5;

FIGS. 9A-9E illustratively provide an example embodiment of a computer program routine for implementing aspects of a decision support tool including determining microbiota serial abundances rarefaction, phylogenetic distance calculation, time-oriented MANOVA, and Hurst-Kolmogorov trend testing, which may utilize the method of FIG. 2, in accordance with an embodiment of the disclosure;

FIG. 10A illustratively provides an example computer program routine for performing rank abundance distribution fitting for determining alpha or UniFrac diversity metric; in accordance with an embodiment of the disclosure;

FIG. 10B illustratively provides an example computer program routine for performing MANOVA, in accordance with an embodiment of the disclosure; and FIG. 10C illustratively provides an example computer program routine for determining the presence of a change or trend (pattern) in the microbiota *Faecalibacterium prausnitzii* (*F. prausnitzii*) abundance.

DETAILED DESCRIPTION

Figure 1A:
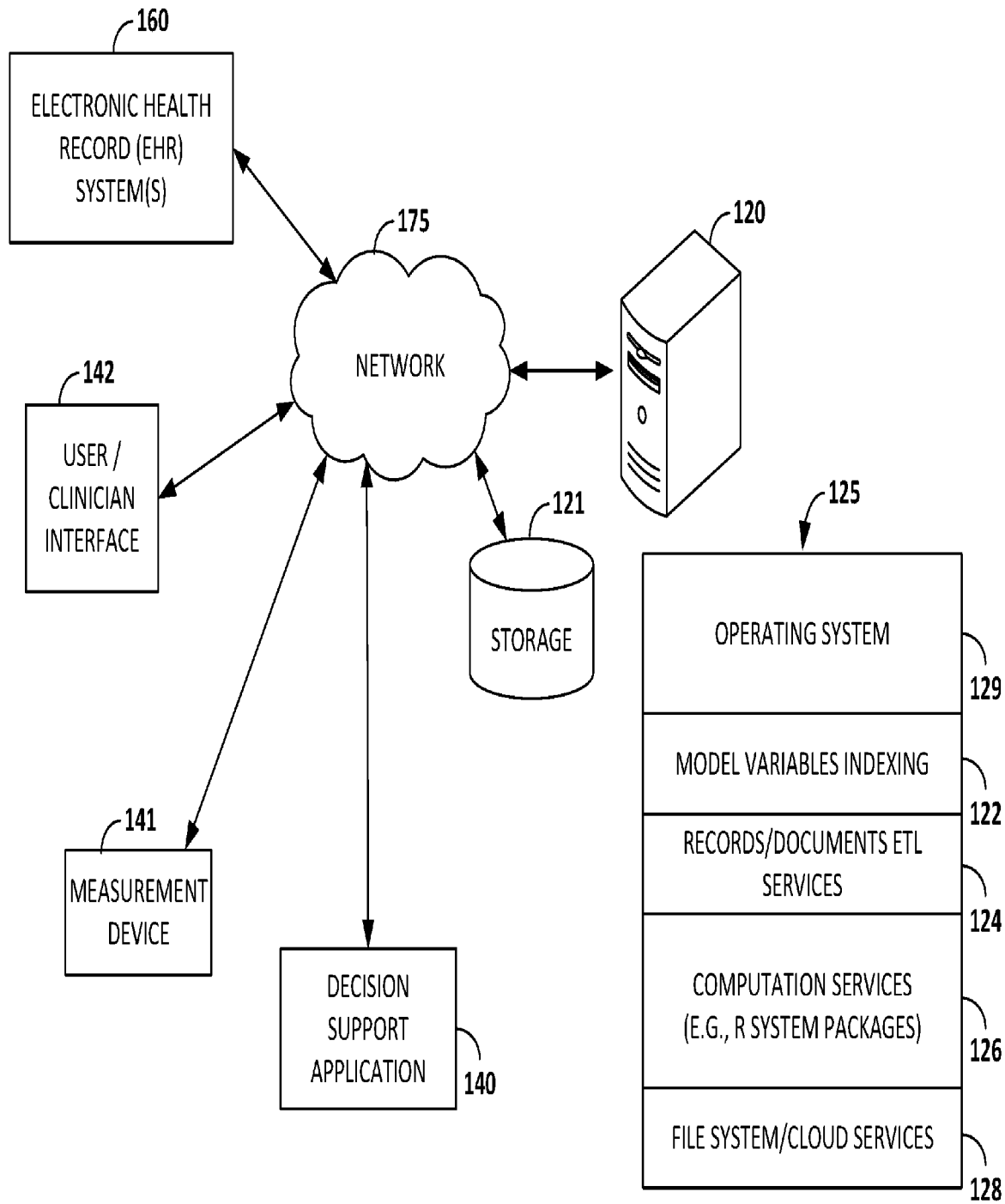
FIGS. 1A and 1B depict aspects of an illustrative operating environment suitable for practicing an embodiment of the disclosure.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of our invention may be embodied as, among other things: a method, system, or set of instructions embodied on one or more computer readable media, which is described herein. Accordingly, the embodiments may take the form of a hardware embodiment, a software embodiment, or an embodiment combining software and hardware. In one embodiment, the invention takes the form of a computer-program product that includes computer-usable instructions embodied on one or more computer readable media.

At a high level, this disclosure describes, among other things, technologies for an improved decision support tool for detecting (and treating human patients based on) changes or trends in microbiota-related activity of the patient. In one example embodiment, a decision support tool determines or receives a longitudinal pattern of relative abundances or diversity levels of microbiota, and automatically analyses this data to detect the occurrence of alternations or trends, which may indicate or be related to meaningful clinical events, such as a change in condition for the patient. The decision support tool may further initiate an action based on a detected change or trend, such as by way of example and without limitation, generating an electronic notification and providing the electronic notification to the patient or caregiver, modifying a treatment program, providing a recommendation, automatically allocating health care resources to the patient, or automatically scheduling a consultation with a caregiver. In some embodiments, the electronic notification may further include statistically robust quantitative interpretations of the patterns or pattern changes. In some embodiments, the decision support tool comprises (or may be embodied as) a smart sensor system that senses or receives serial of microbiota data (or successive measurements of microbiota data) about a human patient and detects the changes or trends. In some embodiments, smart sensor uses the machine learning classification, such as described herein, for detecting or responding to the clinically significant changes or trends.

According to one aspect and as further described herein, serial or successive specimens are acquired from an anatomical site (such as genitals or skin or pharynx) or specimen type (such as feces or blood or sputum) of a subject, such as a human patient or animal. From these specimens, abundances of microbial and/or taxa are measured, and from the serial or successive samples, a time series is formed. In an embodiment, 16S rRNA sequencing methods are utilized, which may include amplification, depending on the total count of organisms in the specimens and the efficiency of nucleotide extraction. Some embodiments may begin by determining or receiving measurement data from the specimens.

The determined taxa abundance and metadata may be stored until enough samples are acquired to comprise a time series of sufficient length, which may be predetermined or based on a particular condition of the subject, a treatment, as described herein. Upon determining a time series of sufficient length, then the taxa may be filtered to retain genera-level taxa having abundance greater than a threshold value, such as 0.05% according to one example embodiment actually reduced to practice and described herein.

Next, a statistical rank-abundance distribution fitting is performed, in some instances, to assure taxa abundance quality. In some embodiments, a phylogenetic tree matrix is determined with distance metric. In particular, the genetic distance may be determined using the Kimura 2-parameter (K80) model. Rarefaction then may be performed on each sample's taxa abundances thereby normalizing counts to a standard count N, such as 10,000 in the example embodiment actually reduced to practice and described herein.

An alpha or UniFrac diversity time series is determined such as by calculating a generalized phylogenetic-distance UniFrac diversity for each time series member. The UniFrac diversity may be variance-adjusted. A condition-related taxa abundance time series then may be determined.

An association of diversity with treatment-epoch also may be determined to ascertain the statistical significance of treatment epoch-related effect on microbiota diversity between the sampled epochs. In some embodiments, a distance-based multivariate analysis of variance (MANOVA) may be performed on diversity time series in relation to the treatment metadata, as a grouping variable. Additionally, one or more time-series trend metrics may be determined to ascertain a statistical significance of time-related effects on the condition-related taxon or taxa. In some embodiments, an abundance time series trend analysis is performed on the one or more condition-related taxa pertinent to the subject's health condition.

In some embodiments, a determination of joint significance of microbiota diversity change statistical significance and taxa abundance change statistical significance is next performed. In this way, data from these statistical significance determinations may be combined to synthesize an interpretation as to the presence of statistically significant microbiota change relevant to the health condition of interest. Where joint significance is determined then a decision support tool running may initiate an intervening action, as described herein.

In this way, embodiments described herein facilitate improved decision support such as prognosis, progression of illness, or treatment effectiveness, for patient conditions that cause alterations in the composition of the intestinal bacterial communities, such as obesity, inflammatory bowel disease (IBD), diabetes, and a variety of disease states.

Figure 3A:
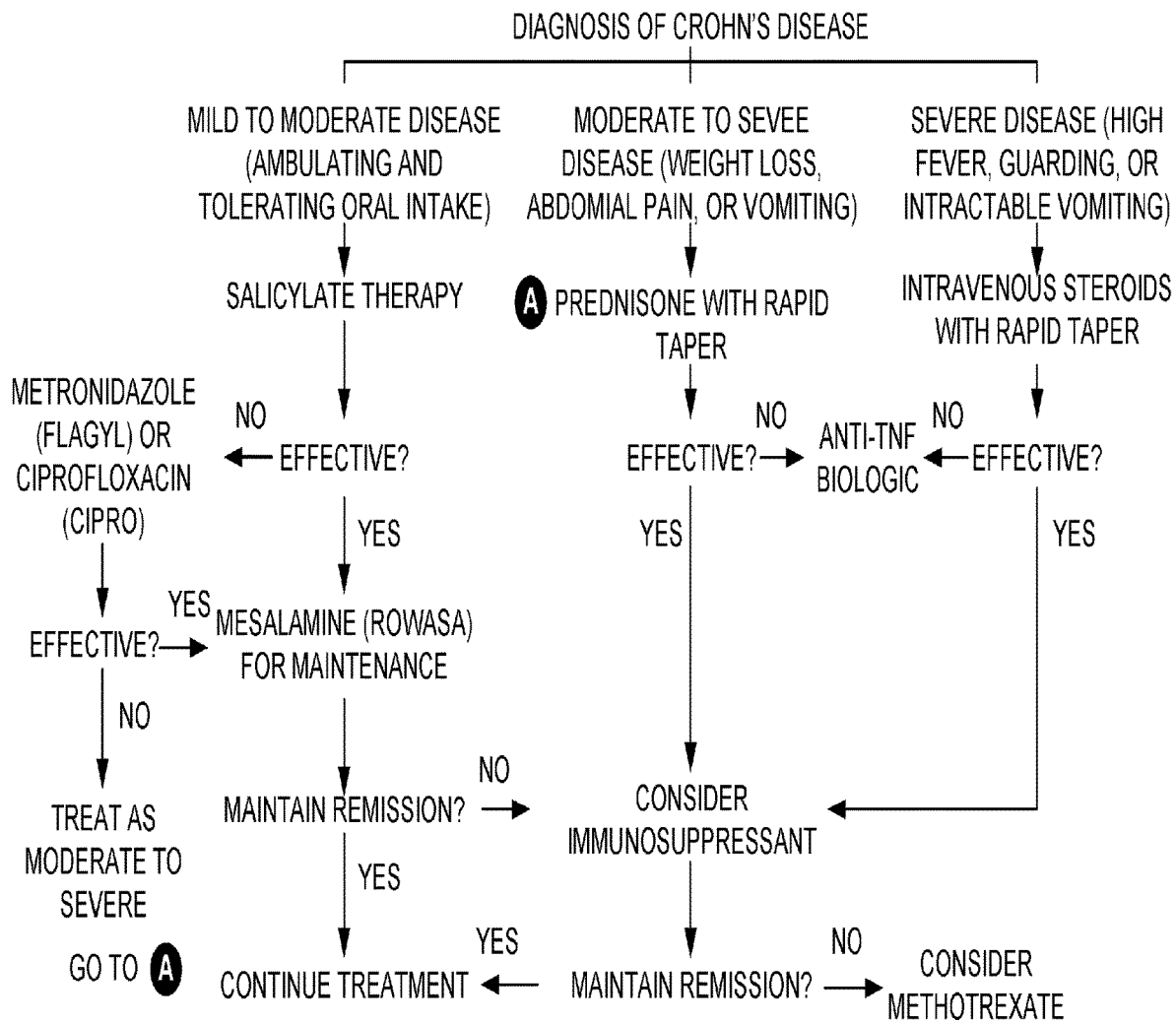
FIGS. 3A and 3B depict treatment protocols for Crohn's Disease and Ulcerative Colitis, respectively.
Figure 3B:
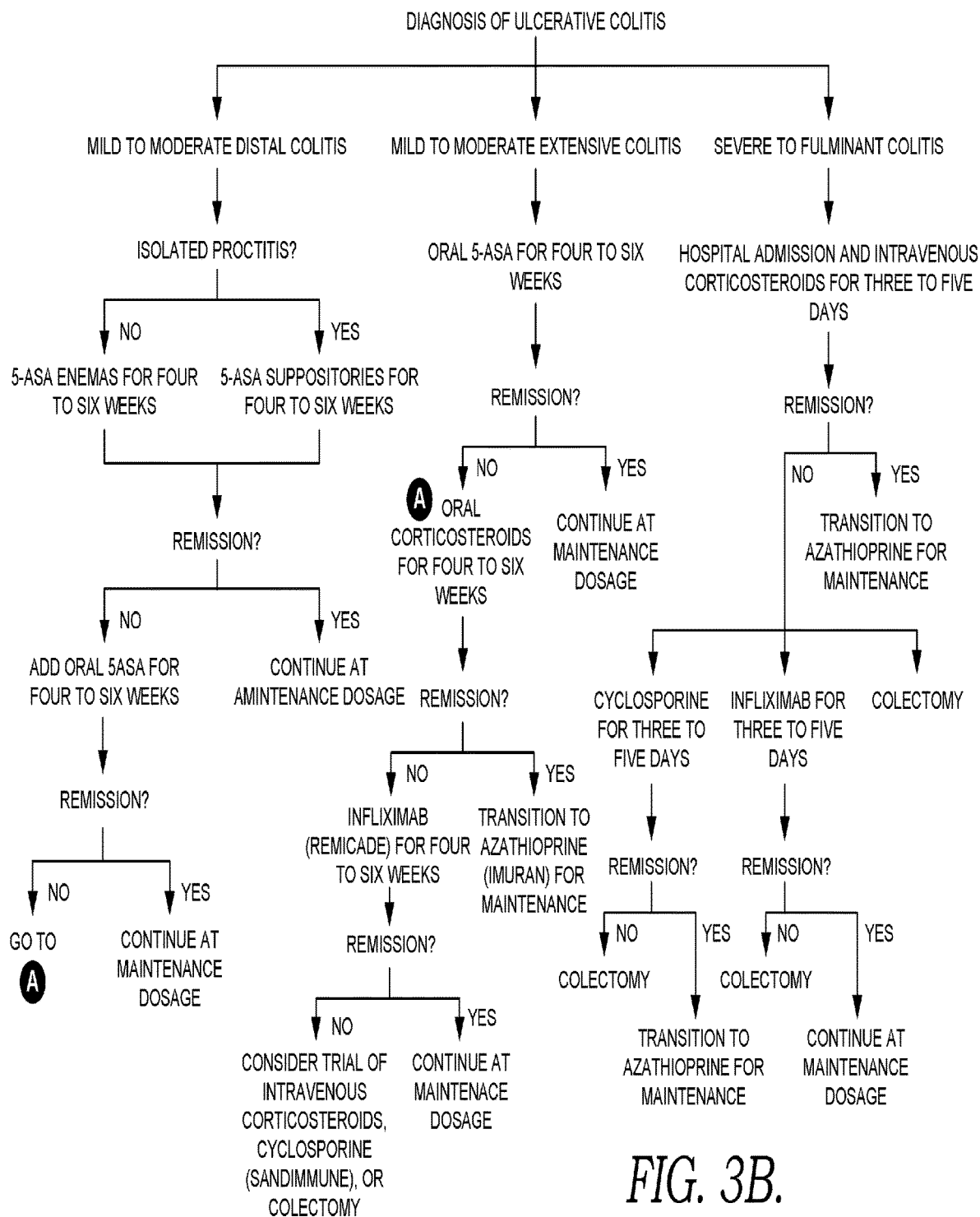
Figure 4:
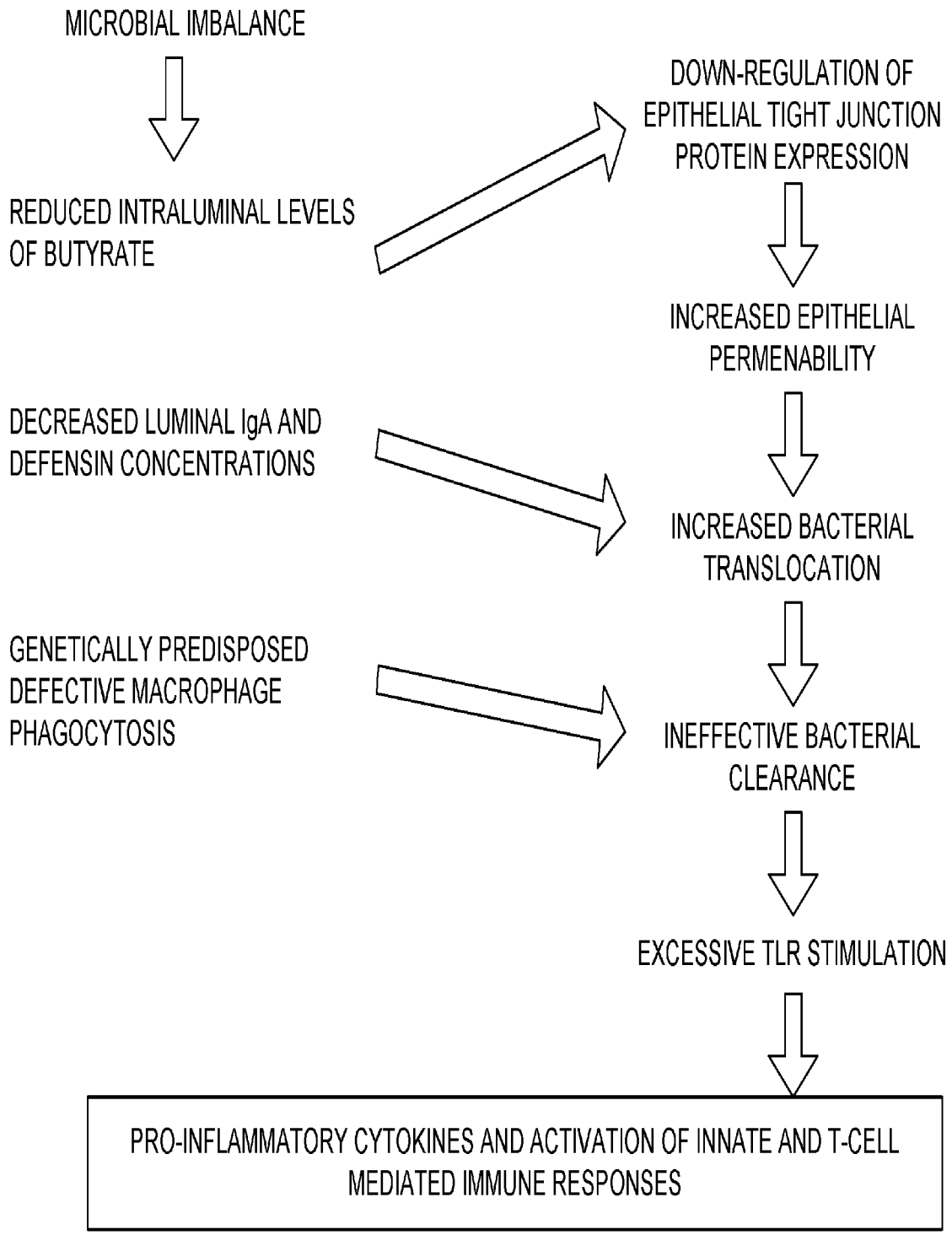
FIG. 4 depicts mechanisms of microbiota action in inflammatory bowel disease (IBD)

For example, IBD, including ulcerative colitis and Crohn's disease, comprises a family of chronic and relapsing inflammatory disorders of the intestine. Although the incidence of IBD is increasing globally, the precise etiology remains unclear. Medical management of IBD is complex, costly, and has variable effectiveness, such that the medication regimen must be adjusted in a personalized fashion so as to discover which medications can modify the course of the disease for each individual. FIGS. 3A and 3B depict the treatment protocols for Crohn's Disease and Ulcerative Colitis, respectively. The most accepted hypothesis of IBD pathogenesis is that complex interactions between genetics, environmental factors, and the host immune system lead to aberrant immune responses and chronic intestinal inflammation. Recent advances in next-generation sequencing technology have identified alteration of the composition and function of the gut microbiota, which is referred to as dysbiosis, in IBD. FIG. 4 depicts mechanisms of microbiota action in inflammatory bowel disease (IBD).

IBD comprises several complex diseases involving genetic and genomics factors, multiple body systems in the affected patient, the microbiota inhabiting the patient's gastrointestinal tract, plus environmental, epigenetic, and other factors. Crohn's disease and ulcerative colitis are prototypical IBD conditions characterized by chronic and heterogeneous manifestations induced by interacting environmental, genomic, microbial and immunological factors. These interactions result in complexity that is inadequately characterized by each pathological component (an '-ome') in isolation without consideration of the interaction among all relevant 'omes that yield an overall 'network effect.' The outcome of this effect is the 'IBD interactome,' defined as a disease network in which dysregulation of individual -omes causes intestinal inflammation mediated by dysfunctional molecular modules. To define the IBD interactome, new concepts and tools, such as provided by the technologies described herein, are needed to implement a systems approach: a data-driven integration strategy that reveals interactions in the system, pinpoints the central drivers of inflammation, and enables management and personalization of targeted therapies. An important component of some embodiments that implement this systems approach is quantitative longitudinal microbiome information to yield a reliable, quantitative basis for managing IBD.

Severe IBD can cause a dramatic dysbiosis of gut microbiota. Changes in host-microbiota interactions in IBD produce dysbioses in which microbiota are less diverse than in healthy persons, or in persons with IBD that is well-controlled. Accordingly, a trend of enriched beneficial bacteria and diminished opportunistic pathogen bacteria may serve as longitudinal prognostic microbiome biomarkers of IBD severity and progression. Additionally, certain elements of therapeutics in IBD are directed to modulating the microbiota to achieve and sustain a microbiome composition having greater diversity of microbial taxa than the microbiome in basal untreated or under-treated conditions.

Understanding the basal gut bacterial community structure and the host metabolic composition, including changes and trends, is pivotal for the interpretation of treatments' longitudinal effects on microbiota, aimed at ameliorating untoward host-microbe interactions. Embodiments of the technologies described herein, including the decision support tool and smart sensor, are able to not only detect these changes and trends, and thus facilitate this understanding, but to automatically respond by initiating an appropriate intervening action. For example, basal time-period colonic microbiota of IBD patients do not resemble the microbiota in healthy controls based on the analysis of Shannon diversity or generalized UniFrac distance diversity metrics. Embodiments may utilize this newly discovered biomarker to provide an improved tool for more effectively detecting, monitoring, and facilitating treatment of patients suffering from IBD.

Similarly, with regard to Crohn's disease, following a flare of Crohn's disease symptoms, fecal microbiota dysbiosis is detected in the gut microbiota in severely symptomatic Crohn's Disease patients, then it gradually resolves. The biodiversity of gut bacteria is initially decreased, and then generally returned to near-normal levels. In addition, at the early stage (from 2 to 4 weeks), many patients' gut microbiota contain opportunistic pathogenic genera *Enterococcus* and *Escherichia*; after effective treatment, the majority is a beneficial genus, *Bacteroides*.

Evidence indicates that the gut microbiota and/or interactions between the microbiota and the host immune system are involved in the pathogenesis of inflammatory bowel disease (IBD). Strategies that target the microbiota have emerged as potential therapies and, among these, probiotics have gained increasing attention. Data derived from animal models of IBD have revealed the potential of several bacterial strains to modify the natural history of IBD. However, thought there is some evidence for efficacy in ulcerative colitis but, to date, there has been little indication that probiotics exert any benefit in Crohn's disease. VSL #3™ (a high-potency probiotic medical food containing eight different strains of bacteria) exhibits benefits in treating ulcerative colitis, and gut microbial diversity is reduced after treatment with VSL #3™. The effect of fecal microbiome transplantation on IBD is controversial. Increasing microbial diversity compared with impaired handling of bacteria presents a dilemma. Antibiotics are the strongest factors in the reduction of microbiome ecological diversity. Some antibiotics may help to induce remission of the disease. Microbiome alteration has been suggested to be an intrinsic property of IBD and a potential predictor in diagnosis and prognosis. However, the effects of therapeutic modulations are variable, and vigilant monitoring of symptoms and longitudinal changes in microbiota biomarkers can help to guide rational, effective therapy.

In regard to longitudinal monitoring, if microbial load varies substantially between samples, then relative profile comparisons are not reliable and may thwart attempts to link microbiome features to quantitative data such as physiological parameters or qualitative data such as symptom scores. Taxa relative-abundance approaches ignore the possibility that altered overall absolute microbiota abundance could be a key identifier of a disease-associated ecosystem configuration. Accordingly, to enable reliable characterization of host-microbiota interactions, microbiome the technologies should be capable of providing not only analysis of rarefacted abundance ratios but also absolute abundance counts.

Some studies have found that in IBD patients compared to healthy controls there is an abnormal colonization of the ileal mucosa by Adherent/Invasive *E. coli* (AIEC) and reduced gut concentrations of *Faecalibacterium prausnitzii*. This condition can be associated to severity of ileal disease and is predictive of high risk for flaring of Crohn's disease. Additionally, a molecular subset of *Bacteroides fragilis*, termed enterotoxigenic *B. fragilis* has been identified in abnormal concentrations in patients with active IBD. Some studies have detected species-specific biases in transcriptional activity, revealing predominant transcription of pathways by individual microorganisms per host (for example, by *Faecalibacterium prausnitzii*). Thus, a loss of these organisms in disease may have more far-reaching consequences than suggested by their genomic abundances. Furthermore, out work has identified organisms that were metagenomically abundant but inactive or dormant in the gut with little or no expression (for example, Dialister invisus). Finally, certain disease-specific microbial taxa exhibit wide abudance variability in patients with IBD (for example, *Bacteroides vulgatus* and *Alistipes putredinis*) in a fashion that may interfere with traditional statistical tests for trends.

As described above, embodiments of the decision support tool described herein improve upon conventional sensors and technologies for detecting, ascertaining or treating patients based on, changes or trends in microbiota-related activity. For example, some of the improvements realized include that these embodiments of the decision support tool are not susceptible to biases, are more tolerant, such as tolerant of variable total bacteria count and relative OTU abundances from specimen to specimen. Additionally some embodiments of our decision support tool can further take advantage of longitudinal trends and host-microbiome interactions' causation of trends to provide enhanced detection, monitoring, or other decision support.

In contrast, the conventional technologies have a number of limitations and problems that are overcome by embodiments of the decision support tool or smart sensor described herein. For instance in contrast to embodiments of the technologies described herein, (1) conventional technologies for measurement and analytics emphasize single-specimen determination of microbiota present in a single sampled body site in a patient and thus do not even provide means for quantitative interpretation of longitudinal microbiota changes, if any, between members of a succession of specimens serially collected from the body site from the patient over a period of time. Additionally, (2) the underlying methods of these technologies are qualitative and typically yield information consisting of graphical displays or descriptive statistics only, which do not reliably direct actions or quantitative interpretations. Furthermore, (3) the methods and equipment utilized by the conventional technologies is complex and not as amenable to automated, cost-efficacious, repeated and ongoing performance.

Additionally, (4) the conventional technologies lack adequate statistical sensitivity to ascertain health condition-related microbiota biomarker indices of exacerbation, remission, and treatment efficacy or non-efficacy, and, therefore, suffer from excessively high false-negative determinations, giving false reassurance regarding individuals in whom time series of health condition-related taxa abundances or microbiota diversity values are in fact exhibiting a temporal shift, trend, or a pattern of variability that relates to the health condition symptoms or treatment efficacy. Similarly, (5) the conventional technologies have inadequate statistical specificity to rule-out conditions having health condition-related microbiota biomarker indices of exacerbation, remission, and treatment efficacy or non-efficacy. These conventional technologies therefore suffers from excessively high false-positive determinations of changes in diversity, health condition-related microbial taxa abundances, or relative-abundance profiles.

These and other deficiencies and limitations of the conventional technologies are mitigated or overcome by the improved technologies described herein. This is because the problems with the conventional technology require new and improved techniques that specifically overcome these drawbacks. Hence, the current embodiments attempt to address these disadvantages by implementing new and improved techniques and features that are not know in conventional industry practice, thereby providing enhanced decision support systems that are capable producing reliable and accurate determinations that have not been previously achieved.

Referring now to the drawings in general, and initially to FIG. 1A in particular, an aspect of an operating environment 100 is provided suitable for practicing an embodiment of the technologies described herein. We show certain items in block-diagram form more for being able to reference something consistent with the nature of a patent specification than to imply that a certain component is or is not part of a certain device. Similarly, although some items are depicted in the singular form, plural items are contemplated as well (e.g., what is shown as one data store might really be multiple data-stores distributed across multiple locations). But showing every variation of each item might obscure the invention. Thus for readability, we show and reference items in the singular (while fully contemplating, where applicable, the plural).

As shown in FIG. 1A, a block diagram is provided showing aspects of an example computing system architecture suitable for implementing an embodiment of this disclosure and designated generally as example operating environment 100. Example operating environment 100 provides an aspect of a computerized system for compiling and/or running aspects of this disclosure including decision support tool and/or smart sensor apparatus, which may be incorporated into a decision support application. For example, in an embodiment, environment 100 may be used for monitoring, detecting or determining, and/or predicting a likely occurrence (or event) or future occurrence (or event) of microbiota-related changes or trends, as described herein, or another condition in a human patient, and additional decision support technology to facilitate caring for patients who may be prone to experience these conditions.

Operating environment 100 is one example of a suitable environment and system architecture for implementing an embodiment of the disclosure. Other arrangements and elements can be used in addition to or instead of those shown, and some elements may be omitted altogether for the sake of clarity. Further, as with operating environment 100, many of the elements described herein are functional entities that may be implemented as discrete or distributed components or in conjunction with other components, and in any suitable combination and location. As described above, some embodiments may be implemented as a system, comprising one or more computers and associated network and equipment, upon which a method or computer software application is executed. Accordingly, aspects of the present disclosure may take the form of an embodiment combining software and hardware aspects that may all generally be referred to herein as a "module" or "system." Further, the methods of the present disclosure may take the form of a computer application embodied in computer readable media having machine-readable application software embodied thereon. In this regard, a machine-readable storage media may be any tangible medium that can contain, or store a software application for use by the computing apparatus.

Computer application software for carrying out operations for system components or steps of the methods of the present disclosure may be authored in any combination of one or more programming languages, including an object-oriented programming language such as Java, Python, R, or C++ or the like. Alternatively, the application software may be authored in any or a combination of traditional non-object-oriented languages such as C or Fortran. The application may execute entirely on the user's computer (i.e., a computing device) as an independent software package, or partly on the user's computer in concert with other connected co-located computers or servers, or partly on the user's computer and partly on one or more remote computers, or entirely on a remote computer or collection of computers. In the latter cases, the remote computers may be connected to the user's computer through any type of network, including a local area network (LAN) or a wide area network (WAN), or the connection may be made to an external computer (for example, via the internet using an Internet Service Provider or ISP) or an arbitrary, geographically-distributed, federated system of computers, such as a cloud-based system.

Moreover, the components of operating environment 100, functions performed by these components, or services carried out by these components may be implemented at appropriate abstraction layer(s) such as the operating system layer, application layer, hardware layer, etc., of the computing system(s). Alternatively, or in addition, the functionality of these components and/or the embodiments described herein can be performed, at least in part, by one or more hardware logic components. For example, and without limitation, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc. Additionally, although functionality is described herein with regards to specific components shown in example operating environment 100, it is contemplated that in some embodiments functionality of these components can be shared or distributed across other components.

Environment 100 includes one or more electronic health record (EHR) systems, such as EHR system(s) 160 communicatively coupled to network 175, which is communicatively coupled to computer system 120. In some embodiments, components of environment 100 that are shown as distinct components may be embodied as part of or within other components of environment 100. For example, EHR system(s) 160 may comprise one or a plurality of EHR systems such as hospital EHR systems, health information exchange EHR systems, clinical genetics/genomics systems, ambulatory clinic EHR systems, psychiatry/neurology EHR systems, and insurance, collections or claims records systems; and may be implemented in or as a part of computer system 120. Similarly, EHR system(s) 160 may perform functions for two or more of types of EHR systems (not shown). EHR system(s) 160 also may include records of physiological variables (such as vital signs measurements) obtained via one or more measurement apparatus, tests, or screenings, such as measurement device 141.

In some embodiments of the technologies described herein, aspects of a decision support tool for patients having or at risk for developing a condition or event occurrence, such a change or trend in microbiota-related activity, as described herein, or recurrence of a condition or event may utilize data about a population of patients derived from patient EHR or other records information. In particular, presently certain data warehouses are created for purposes of public health and observational research purposes and are derived from electronic health records repositories in such a way that they are de-identified so as to comply with applicable confidentiality laws and regulations. The Cerner Health Facts™ data warehouse is such a system that has been curated for more than 15 years. It comprises a large 'transaction database' where each entry corresponds to a patient's 'basket' (a collection of items recorded or transacted at points in time during episodes of care services provisioning in the contributing health care institutions). Each database entry is ordered by the date-time of the transaction. Transaction sequencing is implemented by grouping medical events occurring in the same 'epoch' for the same patient together into 'baskets' and ordering the 'baskets' of each patient by the date-time stamps where the events occurred. Epoch durations may differ according to the age of the patient, or the acute or chronic nature of the health conditions that pertain to the patient, or the rate of change of the severity of the health conditions, or other factors, Epoch durations may be as short as a few minutes (as in critical care ICU or operating room contexts) or may be as long as 10 years or more (as in chronic ambulatory care-sensitive conditions, ACSCs).

Continuing with FIG. 1A, network 175 may comprise the Internet, and/or one or more public networks, private networks, other communications networks such as a cellular network, or similar network(s) for facilitating communication among devices connected through the network. In some embodiments, network 175 may be determined based on factors such as the source and destination of the information communicated over network 175, the path between the source and destination, or the nature of the information. For example, intra-organization or internal communication may use a private network or virtual private network (VPN). Moreover, in some embodiments items shown communicatively coupled to network 175 may be directly communicatively coupled to other items shown communicatively coupled to network 175.

In some embodiments, operating environment 100 may include a firewall (not shown) between a first component and network 175. In such embodiments, the firewall may reside on a second component located between the first component and network 175, such as on a server (not shown), or reside on another component within network 175, or may reside on or as part of the first component.

Embodiments of electronic health record (EHR) system(s) 160 include one or more data stores of health-related records, which may be stored on storage 121, and may further include one or more computers or servers that facilitate the storing and retrieval of the health records. In some embodiments, EHR system(s) 160 and/or other records systems may be implemented as a cloud-based platform or may be distributed across multiple physical locations. EHR system(s) 160 may further include record systems, which store real-time or near real-time patient (or user) information, such as wearable sensor or monitor, support-surface, bedside, laboratory, or in-home patient monitors or sensors, for example, such as measurement device 141.

Example operating environment 100 further includes a user/clinician interface 142 and decision support application 140, each communicatively coupled through network 175 to an EHR system 160. Although environment 100 depicts an indirect communicative coupling between interface 142 and decision support application 140 with EHR system 160 through network 175, it is contemplated that an embodiment of interface 142 or decision support application 140 are communicatively coupled to EHR system(s) 160 directly. For example, in one embodiment a decision support application 140 operating at least in part on a client device (such as a user-operated computer device like a tablet) includes an interface 142 (which may comprise a graphical user interface), which may be used for accessing patient information from an EHR system(s) 160.

An embodiment of decision support application 140 comprises a software application or set of applications (which may include programs, routines, functions, or computer-performed services) residing on a client computing device (or distributed in the cloud and on a client computing device) such as a personal computer, laptop, smartphone, tablet, or mobile computing device. In an embodiment, the application is a Web-based application or applet, and may be used to provide or manage user services provided by an embodiment of the technologies described herein, which may be used by a caregiver or screener to provide, for example, information about the likelihood of a specific patient or population of patients to have or develop a condition or health event, such a change or trend in microbiota-related activity, as described herein, and may further include a degree or level characterizing the severity of the condition or event. In some embodiments, decision support application 140 includes or is incorporated into a smart sensor or computerized decision support tool, as further described herein. Further, some embodiments of decision support application 140 utilize user/clinician interface 142.

In some embodiments, decision support application 140 and/or interface 142 facilitates accessing and receiving information from a user or health care provider about a specific patient or set of patients, according to the embodiments presented herein. Embodiments of decision support application 140 also may facilitate accessing and receiving information from a user or health care provider about a specific patient, caregiver, or population including historical data; health care resource data; physiological variables or other patient-related measurements, time series, and predictions (including plotting or displaying the determined outcome and/or issuing an alert) described herein; or other health-related information, and facilitates the display of results, recommendations, or orders, for example. In an embodiment, decision support application 140 also facilitates determining, receiving, or providing: notifications, recommendations, care plan changes, or orders, staffing scheduling, and/or queries from a user, which may be based on the results of monitoring and/or forecasted outputs, and which may in some embodiments utilize user interface 142. Decision-Support application 140 may also be used for providing diagnostic services or evaluation of the performance of various embodiments.

In some embodiments, user/clinician interface 142 may be used with decision support application 140, such as described above. One embodiment of user/clinician interface 142 comprises a user interface that may be used to facilitate access by a user (including a clinician/caregiver such as a medical caregiver, physical therapist, or the like) to a probability, likelihood, forecast, score or prediction determined according to the technologies described herein, including information indicating a likelihood that a patient is undergoing a meaningful change or trend in microbiota-related activity, as described herein. One embodiment of interface 142 takes the form of a graphical user interface and application, which may be embodied as a software application (e.g., decision support application 140) operating on one or more mobile computing devices, tablets, smartphones, front-end terminals in communication with back-end computing systems, laptops, or other computing devices. In an embodiment, the application comprises or operates in conjunction with the PowerChart® software manufactured by Cerner Corporation. In an embodiment, interface 142 includes a Web-based application (which may take the form of an applet or app) or set of applications usable to manage user services provided by an embodiment of the technologies described herein.

In some embodiments, interface 142 may facilitate providing the output of the determined detections, analysis, measurements, forecast(s), probabilities (or score), recommendations, scheduling orders, providing instructions (such as measuring, recording, and/or otherwise obtaining vital signs or other physiological variable measurements), confirmations or notifications (which may include, for example, confirmation that information has been received or notifications that information has not been received and there may be an error in the measuring instrument, user operation of a measurement device, or measurement procedure), reminders (such as notifications to obtain a physiological measurement sample), or outputs of other actions described herein, as well as logging and/or receiving other feedback from the user/caregiver, in some embodiments. In an embodiment, interface 142 also facilitates receiving orders for the patient from the clinician/user, based on the results of monitoring and predictions. Interface 142 also may be used for facilitating diagnostic services or evaluation of the performance of various embodiments.

Example operating environment 100 includes measurement device 141 communicatively coupled through network 175 to an EHR system 160. In an embodiment, measurement device 141 (sometimes referred to herein as an patient-interface component) comprises one or more sensor components operable to acquire clinical or physiological information about a patient, such as various types of physiological measurements, physiological variables, or similar clinical information associated with a particular physical or mental state of the patient, which may comprise input data into a classifier component of a decision support tool, and which may be acquired periodically, continuously, as needed, or as they become available, and may be represented as one or more time series of measured variables.

In one embodiment, measurement device 141 comprises sensors for obtaining (and in some instances pre-processing or interpreting) measurements of microbiota-related information. In one embodiment, measurement device 141 comprises sensors for obtaining (and in some instances pre-processing or interpreting) non-invasive recording of vital signs or other physiological or patient-related data, which may be obtained continuously, periodically, or at irregular intervals. Accordingly, the term measurement is used broadly herein, and it is contemplated that in some embodiments, measurement device 141 may not perform measurement but may receive information about physiological parameters (such as genotypic or phenotypic information, other measurements such as heart rate (HR), blood pressure (e.g., systolic blood pressure or SBP), respiratory rate (RR), for example and without limitation) which may be measured, observed, or otherwise recorded. Some embodiments of measurement device 141 may comprise one or more sensors, an interface component, and/or processing/communications component (not shown).

For example, in some embodiments, measurement device 141 is a system configured to perform Bacterial rRNA sequencing form extracted nucleotides from acquired specimens, such as fecal matter. The extraction may be performed or facilitated using a DNA extraction kit, such as the Epicentre ExtractMaster™ fecal DNA extraction kits. In one embodiment, measurement device 141 utilizes the Illumina MiSeg™ platform or the Illumina NextSeq 500™ platform for performing the microbiota sequencing. In one embodiment, the sequencing output may be further processed (or pre-processed) using the Illumina BaseSpace™ software. Alternatively, for embodiments utilizing MiSeg™ or NextSeg™, output files may be processed (or pre-processed) with bcl2fastq software. While embodiments are employed using these types of computing systems, the techniques and processes performed by the computing system are a focus of this disclosure, as it is these techniques and processes that realize the improvement over the drawbacks associated with the conventional industry practice.

Figure 5:
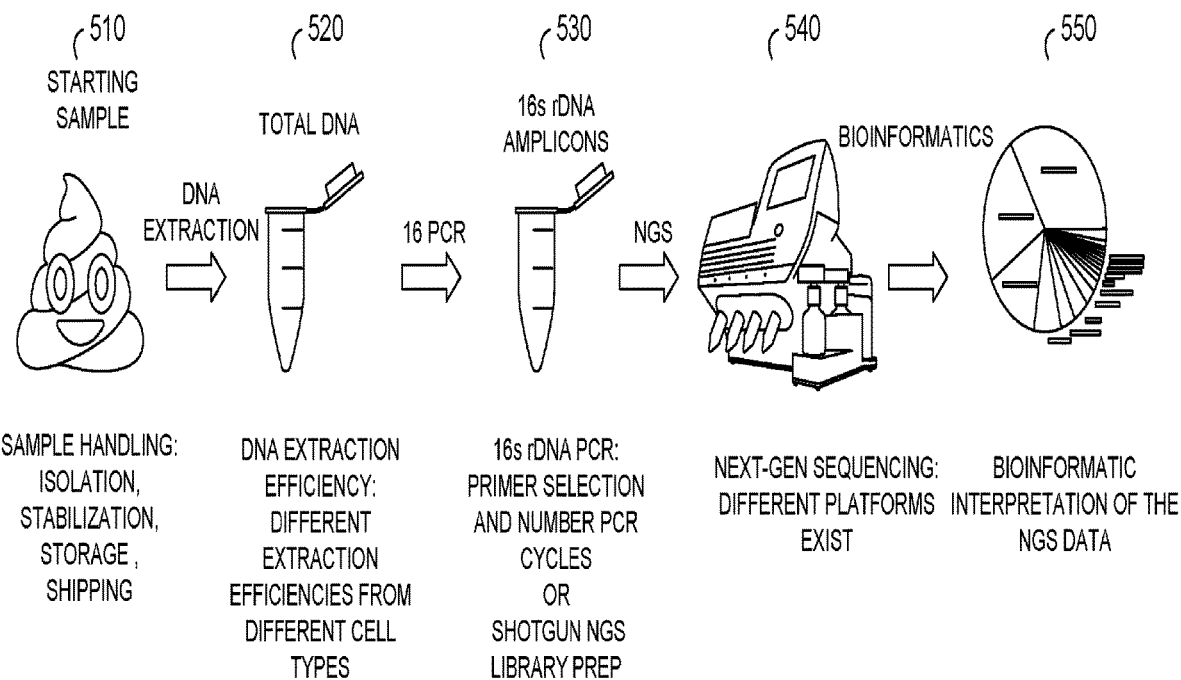
FIG. 5 depicts aspects of a process for 16S rRNA "next generation" sequencing of microbiota from a starting sample, which may be utilized by some embodiments of the disclosure.

FIG. 5 depicts aspects of an example process carried out by an example embodiment of measurement device 141, which is configured as a system for determining bioinformatic information from a starting sample (specimen) according to a process 500. Process 500 starts by receiving a staring sample at step 510. From this specimen, at step 520, DNA extraction is performed. At step 530, 16s rDNA amplicon sequencing (or similar genetic sequencing) may be performed to prepare for Next-Gen sequencing (or similar sequencing or processing) to obtain bioinformatic information provided in step 550. The 16s rDNA amplicon sequencing may comprise a 300-cycle 2×150 bp sequencing. FIG. 6 depicts an example of the 16s rRNA pyrosequencing results, which may be determined as part of the bioinformatics information using process 500 of FIG. 5. In particular, the table depicted in FIG. 6 comprises a table of OTUs and phylogenetic tree data.

Continuing with FIG. 1A, in some embodiments, measurement device 141 may include or utilize a Bluetooth or wireless communication data-transfer capability and may be wirelessly communicatively coupled with an application on a computing device, such as a smartphone an app or aspect of decision support application 140. In some embodiments, measurement device 141 comprises patient bedside monitor, such used in hospital, or a bathroom or toilet monitor, which may be embodied as a smart toilet. In an embodiment, one or more sensor components of measurement device 141 may comprise a user-wearable sensor component or sensor component otherwise integrated into the patient's environment. Examples of sensor components of measurement device 141 include a sensor positioned on an appendage (on or near the user's head, attached to the user's clothing, worn around the user's head, neck, leg, arm, wrist, ankle, finger, etc.); skin-patch sensor; ingestible or sub-dermal sensor; sensor component(s) integrated into the user's living environment (including the bed, pillow, or bathroom); and sensors operable with or through a smartphone carried by the user, for example. It is also contemplated that the clinical or physiological information about patient, such as the monitored variables and/or clinical narratives regarding the patient, used according to the embodiment of the invention disclosed herein may be received from other machine or human-performed (or human-guided) measurements, human observations, or automatically determined by sensors, which may be in proximity to the patient. For example, in one embodiment, a clinician periodically determines microbiota information for the patient and enters the measurement and/or observations via user/clinician interface 142. In another example, a nurse or caregiver enters one or more progress notes for an in-patient via user/clinician interface 142. Similarly, values for other physiological variables or patient data may be entered via user/clinician interface 142.

In addition to the microbiota, other examples of physiological variables monitored by measurement device 141, according to some embodiments, can include vital signs variables, such as heart rate (bradycardia and tachycardia) and blood pressure (hypotension and hypertension), oxygen saturation (peripheral desaturation), other vital signs, or physiologic or patient-related information as described herein, such as treatment regimens, diet, and other microbiota-related data. In some embodiments, microbiota-related information are received by measurement device 141, and may be received or determined from lab results for the patient. In some embodiments these physiological variables monitored by measurement device 141 may include any type of measureable, determinable, or observable physiological or clinical variable or characteristic associated with a patient, which in some embodiments may be used for detecting changes or trends, forecasting a future value (of the measured variable, a composite variable based on one or more measured variables, or other factor determined at least in part from one or more measured variables) of a patient in order to facilitate clinical decision making. In an embodiment, a measurement device 141 comprises a sensor probe and a communication link that periodically transmits identification information and probe data to a decision support application 140, so that a time series of monitored values is stored in a record associated with the patient on an EHR system 160, thereby enabling the decision support application 140 to form a raw binary alarm indication and/or a physiological variable decision statistic.

Embodiments of measurement device 141 may store user-derived data locally or communicate data over network 175 to be stored remotely. Some embodiments of measurement device 141 include a monitor interface, which may be embodied as I/O such as buttons and sounds emitted from the measurement device 141, its firmware or software application or app operating on a user's mobile device or computer system 120, and in an embodiment may facilitate uploading of measured (or recorded, or otherwise received) information from measurement device 141 to computer system 120. Additionally, some embodiments of measurement device 141 include functionality for processing user-derived information locally or for communicating the information to computer system 120, where it is processed. In some embodiments, the processing may be carried out or facilitated by one or more software agents, as described below. In some embodiments the processing functionality, performed on measurement device 141 and/or computer system 120 includes pre-processing and/or signal conditioning, such as removing noise or erroneous information.

Example operating environment 100 further includes computer system 120, which may take the form of one or more servers, and which is communicatively coupled through network 175 to EHR system 160, and storage 121.

Computer system 120 comprises one or more processors operable to receive instructions and process them accordingly, and may be embodied as a single computing device or multiple computing devices communicatively coupled to each other. In one embodiment, processing actions performed by computer system 120 are distributed among multiple locations such as one or more local clients and one or more remote servers, and may be distributed across the other components of example operating environment 100. For example, aspects of decision support application 140 or interface 142 may operate on or utilize computer system 120. Similarly, a portion of computing system 120 may be embodied on user interface 142, decision support application 140, and/or EHR system(s) 160. In one embodiment, computer system 120 comprises one or more computing devices, such as a server, desktop computer, laptop, or tablet, cloud-computing device or distributed computing architecture, a portable computing device such as a laptop, tablet, ultra-mobile P.C., or a mobile phone.

Embodiments of computer system 120 include computer software stack 125, which in some embodiments operates in the cloud, as a distributed system on a virtualization layer within computer system 120, and includes operating system 129. Operating system 129 may be implemented as a platform in the cloud, and which is capable of hosting a number of services such as 122, 124, 126, and 128. Some embodiments of operating system 129 comprise a distributed adaptive agent operating system. Embodiments of services 122, 124, 126, and 128 run as local services or may be distributed across one or more components of operating environment 100, in the cloud, on one or more personal computers or servers such as computer system 120, and/or a computing device running interface 142 or decision support application 140. In some embodiments, interface 142 and/or decision support application 140 operate in conjunction with software stack 125.

In embodiments, model variables indexing (or mapping) service 122 and records/documents ETL service 124 provide services that facilitate retrieving patient variables such as physiological or other measurements, which may include frequent item sets, extracting database records, and/or cleaning the values of variables in records. For example, services 122 or 124 may perform functions for synonymic discovery, indexing or mapping variables in records, or mapping disparate health systems' ontologies, such as determining that a particular medication frequency of a first record system is the same as another record system. Some embodiments of software stack 125 may also include predictive models service (not show), which in general is responsible for providing models such as multi-variable models, for detecting or predicting a particular condition or event utilizing a classifier apparatus to detect a conduction, such as a change or trend in microbiota-related activity. In some embodiments, services 122 and/or 124 may invoke computation services 126.

Computation services 126 may perform statistical software operations, and may include statistical calculation packages such as, in one embodiment, the R system (the R-project for Statistical Computing, which supports R-packages or modules tailored for specific statistical operations, and which is accessible through the Comprehensive R Archive Network (CRAN) at http://cran.r-project.org) or similar services. In an embodiment, computation services 126 and include computer-performed services or routines, which may be embodied as one or more software agents or computer program routines such as the example embodiments of computer program routines illustratively provided in FIGS. 9A-9E and 10A-10C. In one embodiment, computation services 126 comprises the R-System GUniFrac package, for determining generalized UniFrac distances for comparison of microbial communities, and the HKprocess package for determining inferences utilizing the Hurst-Kolmogorov process. Additional details about example computation services 126 are provided in the example computer program routines of 9A-9E and 10A-10C, and described further in connection to FIG. 2.

Computation services 126 also may include natural language processing services (not shown) such as Discern nCode™ developed by Cerner Corporation, or similar services. In an embodiment, computation services 126 include the services or routines, which may be embodied as one or more software agents or computer software routines such as the example embodiments of computer program routines illustratively provided in FIGS. 9A-9E and 10A-10C. Computation services 126 also may include services or routines for utilizing one or more classification models or processes, such as described in connection to FIG. 2 and the example computer program routines illustratively provided in FIGS. 9A-9E and 10A-10C. In some embodiments, computation services 126 use EHR system(s) 160, model data and model storage services (not shown), and/or other components of example operating environment 100, and may also include services to facilitate receiving and/or pre-processing physiological (or other patient-related) data. For instance, model data and model storage services may be utilized to perform services for facilitating storage, retrieval, and implementation of the forecasting models described herein and of the data used in models, classifier apparatus, or predictive services.

In some embodiments, software stack 125 includes file system or cloud-services 128. Some embodiments of file system or cloud-services 128 may comprise an Apache Hadoop and Hbase framework, or similar frameworks operable for providing a distributed file system, and which in some embodiments facilitate provide access to cloud-based services, such as those provided by Cerner Healthe Intent®. Additionally or alternatively, some embodiments of file system or cloud-services 128 or embodiments of software stack 125 may comprise one or more stream processing service(s). For example, such stream processing service(s) may be embodied using IBM InfoSphere stream processing platform, Twitter Storm stream processing, Ptolemy or Kepler stream processing software, or similar complex event processing (CEP) platforms, frameworks, or services, which may include the user of multiple such stream processing services (in parallel, serially, or operating independently). Some embodiments of the invention also may be used in conjunction with Cerner Millennium®, Cerner CareAware® (including CareAware iBus CD), Cerner CareCompass®, or similar products and services.

Example operating environment 100 also includes storage 121 (also referred to as data store 121), which in some embodiments includes patient data for a candidate or target patient (or information for multiple patients), including raw and processed patient data; variables associated with patient diagnoses or determinations, recommendations; recommendation knowledge base; recommendation rules; recommendations; recommendation update statistics; an operational data store, which stores events, frequent item sets (such as "X often happens with Y", for example), and item sets index information; association rule-bases; agent libraries, solvers and solver libraries, and other similar information including data and computer-usable instructions; patient-derived data; and health care provider information, for example. It is contemplated that the term data includes any information that can be stored in a computer-storage device or system, such as user-derived data, computer usable instructions, software applications, or other information. In some embodiments, data store 121 comprises the data store(s) associated with EHR system 160. Further, although depicted as a single storage data store, data store 121 may comprise one or more data stores, or may be in the cloud.

Figure 1B:
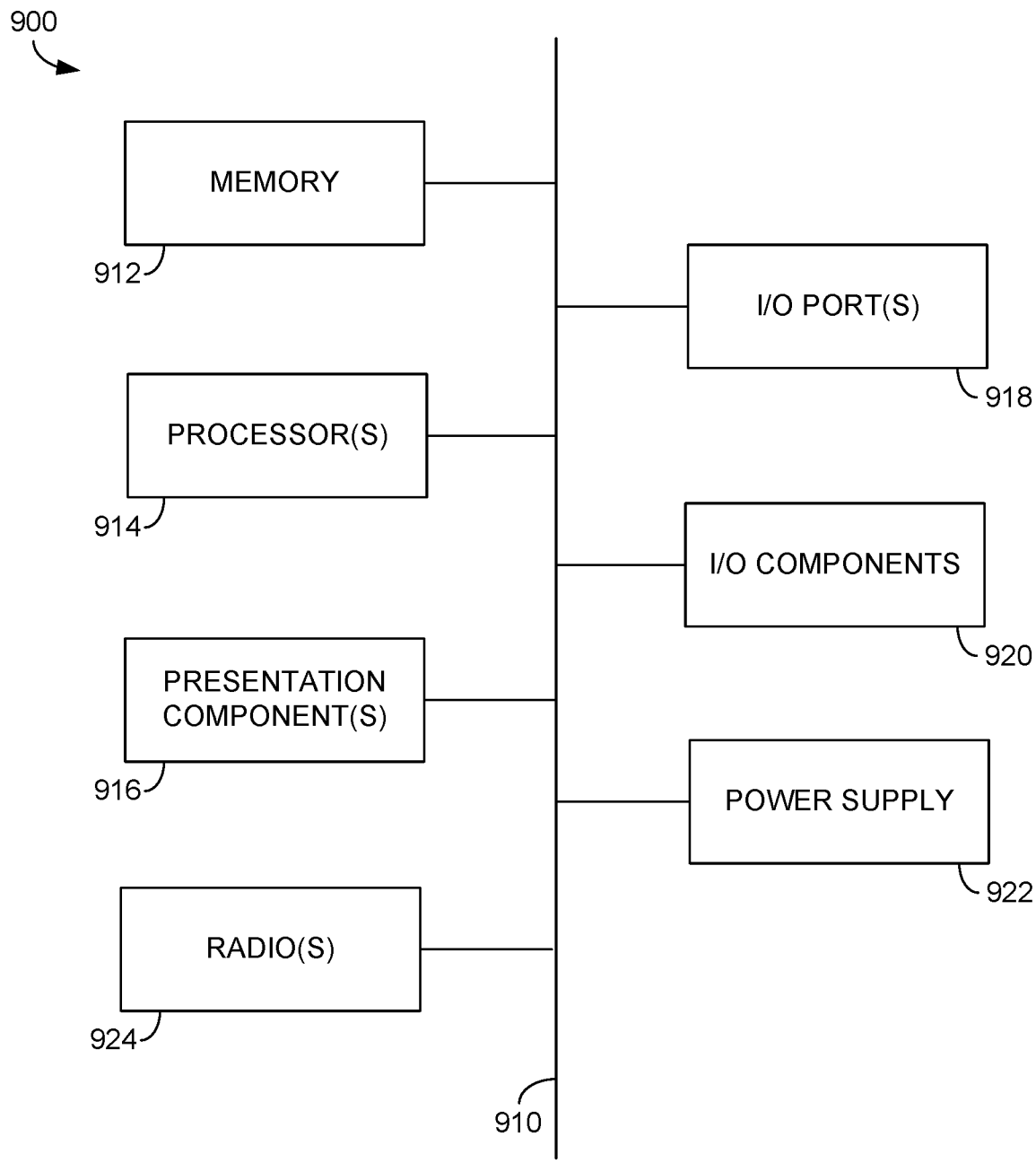

Turning briefly to FIG. 1B, there is shown one example embodiment of computing system 900 representative of a system architecture that is suitable for computer systems such as computer system 120. Computing device 900 includes a bus 910 that directly or indirectly couples the following devices: memory 912, one or more processors 914, one or more presentation components 916, input/output (I/O) ports 918, input/output components 920, radio 924, and an illustrative power supply 922. Bus 910 represents what may be one or more busses (such as an address bus, data bus, or combination thereof). Although the various blocks of FIG. 1B are shown with lines for the sake of clarity, in reality, delineating various components is not so clear, and metaphorically, the lines would more accurately be grey and fuzzy. For example, one may consider a presentation component, such as a display device, to be an I/O component. Also, processors have memory. As such, the diagram of FIG. 1B is merely illustrative of an example computing system architectures that can be used in connection with one or more embodiments of the present disclosure. Distinction is not made between such categories as "workstation," "server," "laptop," "hand-held device," etc., as all are contemplated within the scope of FIG. 1B and reference to "computing system."

Computing system 900 typically includes a variety of computer-readable media. Computer-readable media can be any available media that can be accessed by computing system 900 and includes both volatile and nonvolatile media, and removable and non-removable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing system 900. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above may be included within the scope of computer-readable media.

Memory 912 includes computer-storage media in the form of volatile and/or nonvolatile memory. The memory may be removable, non-removable, or a combination thereof. Exemplary hardware devices include solid-state memory, hard drives, optical-disc drives, etc. Computing system 900 includes one or more processors that read data from various entities such as memory 912 or I/O components 920. In an embodiment, storage 121 is embodied as memory 912. Presentation component(s) 916 present data indications to a user or other device. Exemplary presentation components include a display device, speaker, printing component, vibrating component, etc. In an embodiment, functionality provided via user/clinician interface 142 is facilitated by one or more presentation components 916.

In some embodiments, computing system 924 comprises radio(s) 924 that facilitates communication with a wireless-telecommunications network. Illustrative wireless telecommunications technologies include CDMA, GPRS, TDMA, GSM, LTE, WiMAX, and the like. Radio 924 may additionally or alternatively facilitate other types of wireless communications including Wi-Fi, Bluetooth, NFC, other types of RF communication, light, infrared, or the like. As can be appreciated, in various embodiments, radio 924 can be configured to support multiple technologies and/or multiple radios can be utilized to support multiple technologies.

I/O ports 918 allow computing system 900 to be logically coupled to other devices, including I/O components 920, some of which may be built in. Illustrative components include a microphone, joystick, game pad, satellite dish, scanner, printer, wireless device, etc. The I/O components 920 may provide a natural user interface (NUI) that processes air gestures, voice, or other physiological inputs generated by a user. In some instances, inputs may be transmitted to an appropriate network element for further processing. An NUI may implement any combination of speech recognition, stylus recognition, facial recognition, biometric recognition, gesture recognition both on screen and adjacent to the screen, air gestures, head and eye tracking, and touch recognition (as described in more detail below) associated with a display of the computing system 900. The computing system 900 may be equipped with depth cameras, such as stereoscopic camera systems, infrared camera systems, RGB camera systems, touchscreen technology, and combinations of these, for gesture detection and recognition. Additionally, the computing system 900 may be equipped with accelerometers or gyroscopes that enable detection of motion. While embodiments are employed using these computing systems, the focus of this application is the logical structures programmed into the computing system, since it is the logical structures that are carried out by the computer—not the computer components themselves—that realize the improvement over the drawbacks of the conventional industry practice.

The architecture depicted in FIG. 1B is provided as one example of any number of suitable computer architectures, such as computing architectures that support local, distributed, or cloud-based software platforms, and are suitable for supporting computer system 120.

Returning to FIG. 1A, in some embodiments, computer system 120 is a computing system made up of one or more computing devices. In some embodiments, computer system 120 includes one or more software agents, and in an embodiment includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

Figure 2:
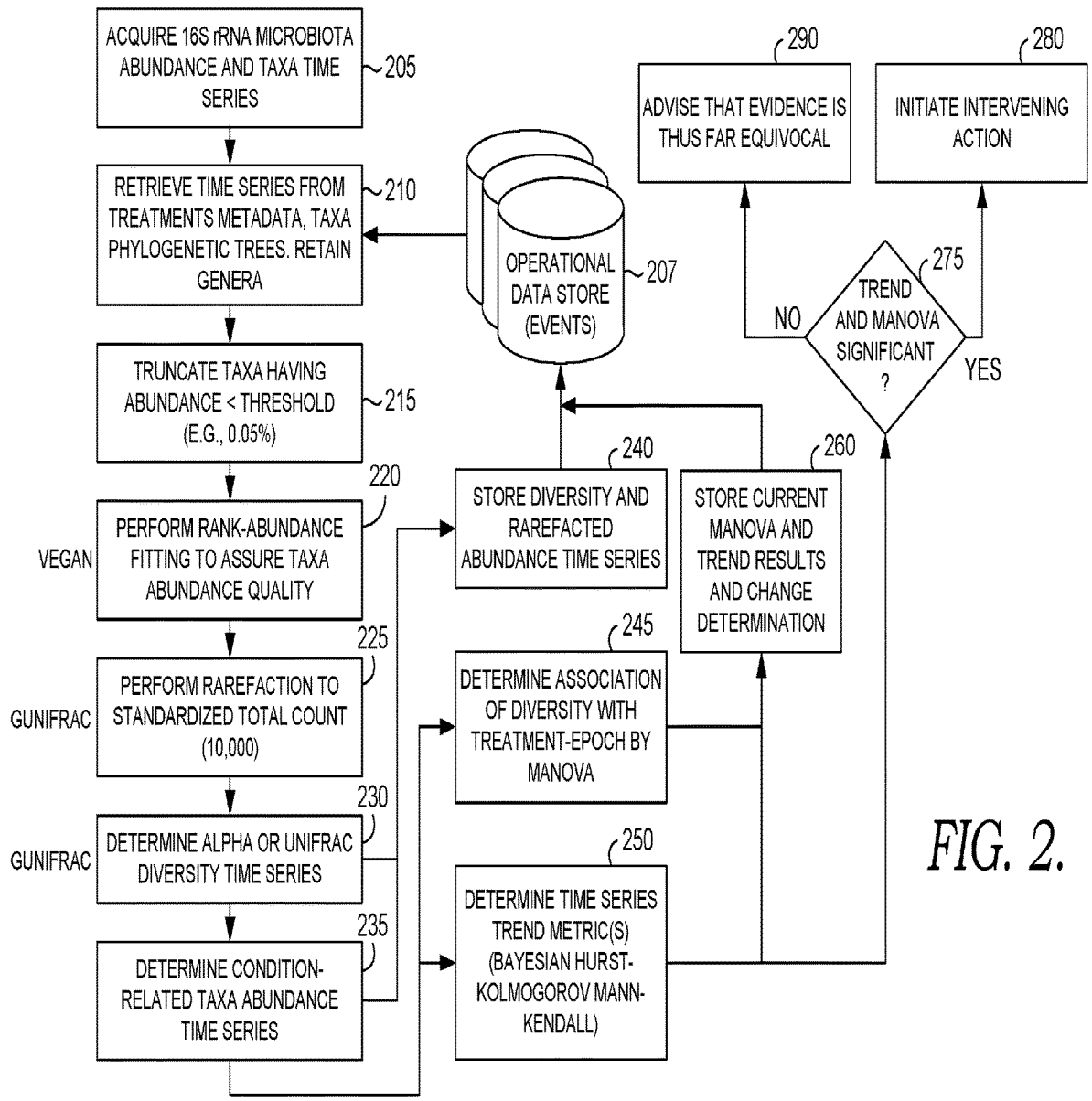
FIG. 2 depicts a flow diagram of a method for determining and monitoring microbiota diversity, detecting a clinically significant alteration or trend, and initiating an action, in accordance with an embodiment of the disclosure.

Turning now to FIG. 2, one example embodiment is provided of a method 200 for conditionally initiating an intervening action based on detecting a clinically significant alteration or trend in microbiota diversity for a subject. In particular, method 200 generates and utilizes an embodiment of an improved smart sensor system for detecting and ascertaining meaningful changes or trends in microbiota-related activity. In some embodiments, the smart sensor system is a component of (or operate in conjunction with) a decision support tool. In one embodiment, the smart sensor comprises a computer-implemented sensor or software-based computerized sensor that utilizes the newly discovered aspects of physiological data of a patient, which may be received from laboratory measurements, and employs a novel process to derive new information from the aspects of physiological data, and then applies a classifier to ultimately detect clinically significant alteration or trend in microbiota diversity.

With reference to FIG. 2, abundance weighted non-phylogenetic diversity measures such as Simpson and Shannon may be utilized in human microbiome methods. But in contrast, abundance-weighted phylogenetic diversity (PD) measures, as utilized by embodiments described in connection to FIG. 2, would not be typically utilized for this purpose. Abundance-weighted PD measures take a sum of branch lengths weighted by abundance, such that branches that connect abundant taxa get a higher weight than ones that do not. Thus, rare taxa and contaminant sequences are down-weighted compared with abundant taxa. The level of similarity between samples or groups of samples is called beta diversity. As with alpha diversity, classical measures applied to OTU counts may be used; however, phylogenetics-based methods may be utilized, and may be variants of the "UniFrac" PD metric.

In some embodiments, a generalized UniFrac distance is utilized. The weighted version of the UniFrac metric accounts for the relative abundance of each of the taxa within the communities, but this places too much emphasis on the most abundant taxa. The unweighted version of the UniFrac metric places too much emphasis on rare taxa or specimen contaminants. By contrast, the generalized UniFrac distance corrects the limitation of the weighted and unweighted UniFrac metrics by down-weighting their emphasis on abundant and rare taxa, respectively.

Such diversity metrics are sensitive to variable sequencing depth. Therefore, to compare microbiomes on an equal basis, some embodiments of the technologies described herein utilize a rarefaction method prior to determining diversity. Rarefaction curves are utilized for estimating species richness. Raw species richness counts, which are used to create accumulation curves, can be compared when the species richness has reached a clear asymptote. OTU species richness increases with sample size; differences in empirical richness may be caused by differences in sample size. Rarefaction curves produce smoother lines that facilitate point-to-point or full dataset comparisons. One can plot the number of species as a function of either the number of individuals sampled or the number of samples taken. The sample-based approach accounts for patchiness in the data that results from natural levels of sample heterogeneity. However, when sample-based rarefaction curves are used to compare taxon richness at comparable levels of sampling effort, the number of taxa should be plotted as a function of the accumulated number of individuals, not accumulated number of samples, because datasets may differ systematically in the mean number of individuals per sample. One cannot simply divide the number of species found by the number of individuals sampled in order to correct for different sample sizes. Doing so would assume that the number of species increases linearly with the number of individuals present, which is not in general the case.

Rarefaction may assume that the individuals in an environment are randomly distributed, the sample size is sufficiently large, that the samples are taxonomically similar, and that all of the samples have been collected and processed in the same manner. If these assumptions are not met, the resulting curves may be skewed. Rarefaction works well when no taxon is extremely rare or common or when beta diversity is very high. Rarefaction may assume that the detected number of a species reflects the sampling intensity, but if one taxon is especially common or rare, the measured count will be related to the extremity of the number of individuals of that species, not to the intensity of sampling. The technique may not account for specific taxa. It examines the number of taxons present in a given sample, but does not look at which OTUs are represented across samples. Thus, two samples that each contain N species may have substantially different compositions, leading to a biased estimate (under-estimation) of species richness. The technique may not recognize species abundance, but species richness. A better measure of diversity may account for both the number of species present and the relative abundance of each.

The reasons for false-positive and false-negative errors of prior art methods are numerous. It is possible that the health condition may exhibit patterns of spontaneous exacerbation and remission that are unrelated to the course of treatment(s). It is possible that treatment effectiveness may not be manifested immediately but only after a latency period has elapsed. It is moreover possible that treatment effectiveness may fade over time, that compensatory or "escape" responses of the interacting subsystems may supervene in such a manner as to attenuate treatment effectiveness, or that the patient's tolerance for or adherence to the prescribed regimen may wane over time. Furthermore, it is possible that stress or lifestyle alterations or other unmeasured factors may confound interpretation of treatment efficacy across time. Thus, to avoid most such false-positive and false-negative errors and to render reliable interpretations of microbiome biomarkers of treatment effectiveness it is not sufficient to statistically measure the relation of microbiota diversity or symptom score with respect to time alone (trend test) or with respect to treatment regimen alone (MANOVA).

In contract, some embodiments of method 200 entail jointly determining both the relation of microbiota diversity to treatment and the relation of disease-related taxa abundances to time under different treatment regimens. For instance, if both determinations prove to be significant, then the decision support tool may determine the efficaciousness or deleteriousness of the respective time-periods' treatments with regard to the condition being treated and initiate an intervening action, such as emitting a notification, such as an advisory interpretation to that effect. Conversely, if either of the determinations is statistically non-significant, then a assertions of the comparative non-superiority and non-inferiority of the two or more time periods and their respective treatment regimens can be emitted.

Some embodiments of method 200 utilize trend testing. By way of example and not limitation, trend testing may comprise the classical Mann-Kendall trend test, partial Mann-Kendall trend test, multivariate (multi-OTU) Mann-Kendall trend test, Bayesian Mann-Kendall trend test under the scaling hypothesis, linear regression of microbiota diversity with a treatment*time interaction term to determine slope versus time with the slope coefficient's significance assessed by ANCOVA and the F-test, Cox-Stuart trend test, correlated Hirsch-Slack test, Sen's slope, partial Pearson and Spearman correlation trend test, change-point detection tests (Lanzante's test, Pettitt's test, Buishand range test, Buishand U-test, Standard normal homogeneity test), tests for detection of non-randomness (Wallis-Moore phase-frequency test, Bartels rank von Neumann's ratio test, Wald-Wolfowitz test), and the two-sample robust rank-order distributional test.

One aspect utilized by an embodiment a decision support tool utilizing method 200 is that processes of temporal evolution of microbiota in a mammalian subject exhibit a scaling behavior, also known as the Hurst phenomenon. Accordingly an appropriate way to model this behavior is as a Hurst-Kolmogorov stochastic process. A Hurst-Kolmogorov process (HK) entails high autocorrelations even for large lags, as well as high variability even at the scale of the overall body of the subject, or a major subsystem such as the gut. A problem that arises is how to incorporate the observed past microbiota composition data in deriving the predictive distribution of microbiota abundance processes at time scales of weeks or months, much longer than the cell-cycle generation times of the microbiota. One embodiment applies Bayesian techniques to create a framework to solve this problem. Under the constraint where there is no prior information for the parameters of the HK process, we may utilize a non-informative distribution for the Bayesian prior distribution.

The application of HK methods in medical or microbiome applications is heretofore unknown. The scaling hypothesis is proposed for modeling wide variability and the Mann-Kendall test can be adapted to account for the effect of multi-dimensional scaling in microbiota abundance time series. Accordingly, in some embodiments of method 200, the modified Mann-Kendall test is applied to a group of taxa related to the condition of interest (such as IBD) and rarefied abundance time series from basal period and subsequent treatment epochs. The results show a considerable reduction in the number of taxa exhibiting significant trends when the effect of scaling is taken into account. These results indicate that the evidence of real trends in OTU abundance data is highly significant under effective treatments. Applying Bayesian processes to for analyzing taxa diversity or abundances time series as HK processes admitting scaling, helps to minimize or avoid false-negative errors of some conventional trend testing technologies, such as determining statistically significant but opposite trends in some OTUs so that no actionable conclusion can be reached, or determining statistically significant but opposite trends in different segments of the same time series.

Accordingly, method 200 begins at step 205, wherein microbiota abundance and taxa information associated with a subject are received. For instance, serial or successive specimens may be acquired from an anatomical site (such as genitals or skin or pharynx) or specimen type (such as feces or blood or sputum) of a subject, such as a human patient or animal. In one embodiment, the inter-sampling interval is not shorter than the cell-cycle generation time of microbiota in log-phase growth (for instance, 8 to 12 hours) and in some instances, may be at least several times a typical generation time. In the case of excreta, better results may be obtained where the inter-sampling interval is not shorter than the usual residence time of a bolus passing through the length of the viscus (thus for gut, approximately 24 hours).

From the specimens, abundances of microbial and/or taxa are measured, and from the serial or successive samples, a time series is formed. In an embodiment, 16S rRNA sequencing methods are utilized, which may include amplification, depending on the total count of organisms in the specimens and the efficiency of nucleotide extraction. Some embodiments begin by determining or receiving measurement data from the specimens to determine the time series. In some embodiment, the measurements may be received from an electronic health record associated with the patient (such as EHR 160), may be received from lab results or smart sensor or measurement device, such as measurement device 141 (FIG. 1A) for example.

Some embodiments of step 205 further include associating a particular patient with the measurement device 141, system, or data stream, and/or binding information about the patient or patient's EHR and initializing a data.frame (e.g., attributes and current date) for acquiring the microbiota information.

At step 210, retrieve time series from treatments metadata, taxa phylogenetic trees, and retain genera. In embodiments of step 210, the specimens may be associated with a diagnostic health condition of interest in the subject sampled, with one or more taxa pertinent to management of the health condition, and with the subject's treatment metadata (or condition metadata) corresponding to the collection date on which each specimen was acquired. The determined taxa abundance and metadata may be stored until enough samples are acquired to comprise a time series of sufficient length. In one embodiment, a time series of at least 8 specimens is determined. For example, the time series may represent data from at least 4 specimens from each of at least two treatment time periods or epochs that are to be compared. In other embodiments, the time series may comprise 4 specimens, and in some embodiments, fewer specimens may be used (or a shorter time series), but results may be degraded (e.g., resulting in a lower specificity or sensitivity).

At step 215, upon determining a time series of sufficient length, then the taxa may be filtered to retain genera-level taxa having abundance greater than a threshold value. In one embodiment, the threshold value is pre-determined and comprises 0.05%. In another embodiment, the threshold is determined based on the patient's condition, the patient's treatment, or may be set by a clinician or caregiver.

At step 220, statistical rank-abundance distribution fitting is performed. Rank-abundance distribution fitting may be performed, in some instances, to assure taxa abundance quality. In some embodiment, a least-squares method is utilized to perform the fitting. For example, in one embodiment, least-squares may be utilized to fit to a log-normal or Zipf-Mandelbrot distribution. In this way, step 220 may utilized if needed to ascertain that the quality of the measurements of microbial taxa is adequate for subsequent analysis. Some embodiments of step 220 utilize computation services 126, which may include the R-system vegan package, such as shown in the example computer program routine of FIG. 9A-9E.

In some embodiments, method 200 may determine a phylogenetic tree matrix with distance metric. In particular, the genetic distance may be determined using the Kimura 2-parameter (K80) model. For instance, in an embodiment, a phylogenetic tree matrix with may be performed by Unweighted Pair Group Method with Arithmetic Mean (UPGMA) methods on the K80 distance matrix, for the taxa represented in the time series.

Figure 7:
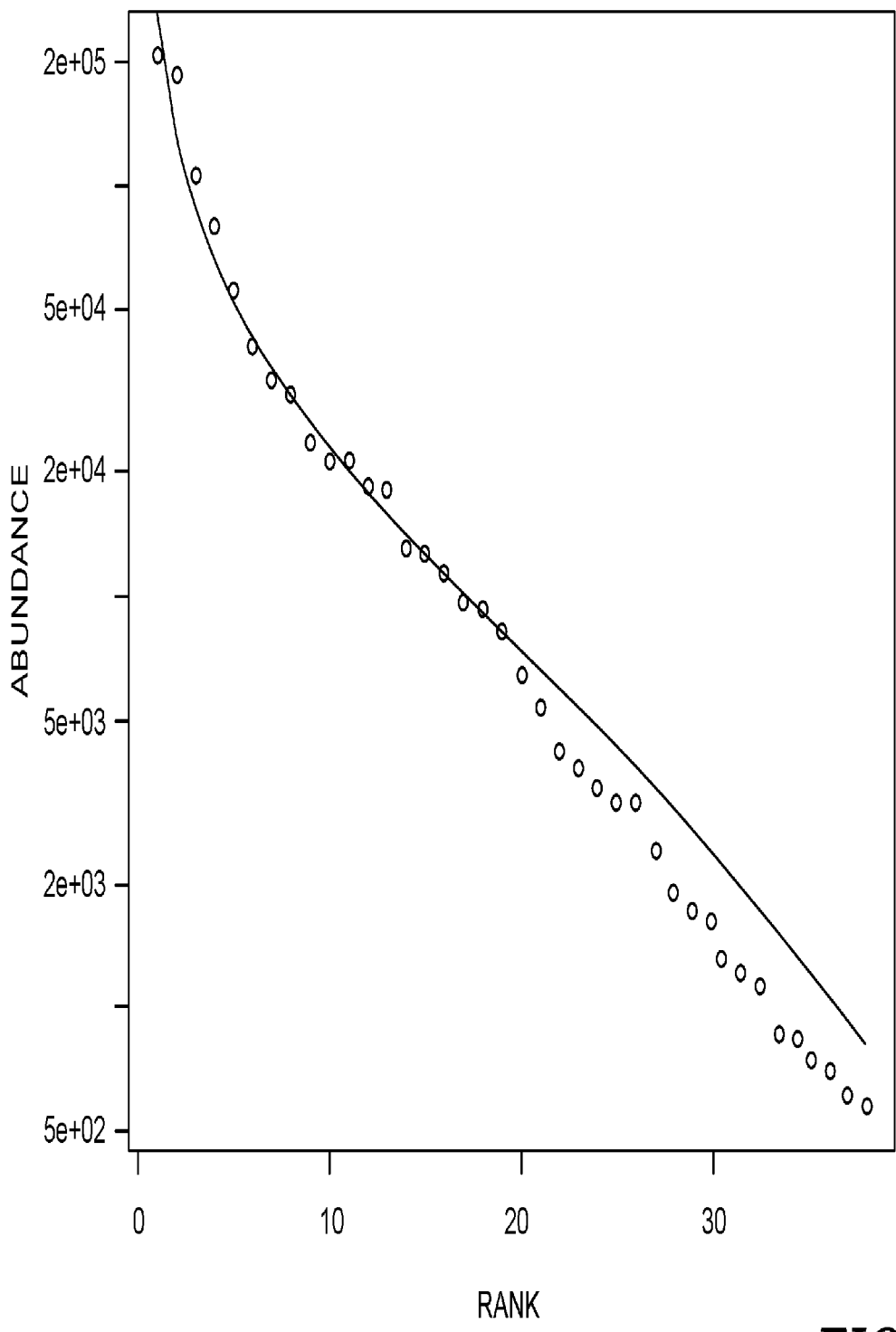
FIG. 7 depicts fit rank-abundance distribution and rarify counts for comparison of alpha diversity and beta phylogenetic diversity among serial specimens, in accordance with an embodiment of the disclosure.

At step 225, rarefaction may be performed on each sample's taxa abundances thereby normalizing counts to a standard count N. In some embodiments, such as in the case of in the case of fecal microbiota time series, N may be approximately 10,000. Some embodiments of step 250 utilize computation services 126, which may include the R-system gunifrac package, such as shown in the example computer program routine of FIG. 9A-9E. An example graph showing aspects of the results of steps 220 and 225 for an embodiment actually reduced to practice, and in particular showing fit rank-abundance distribution and rarify counts, is provided in FIG. 7.

Figure 8:
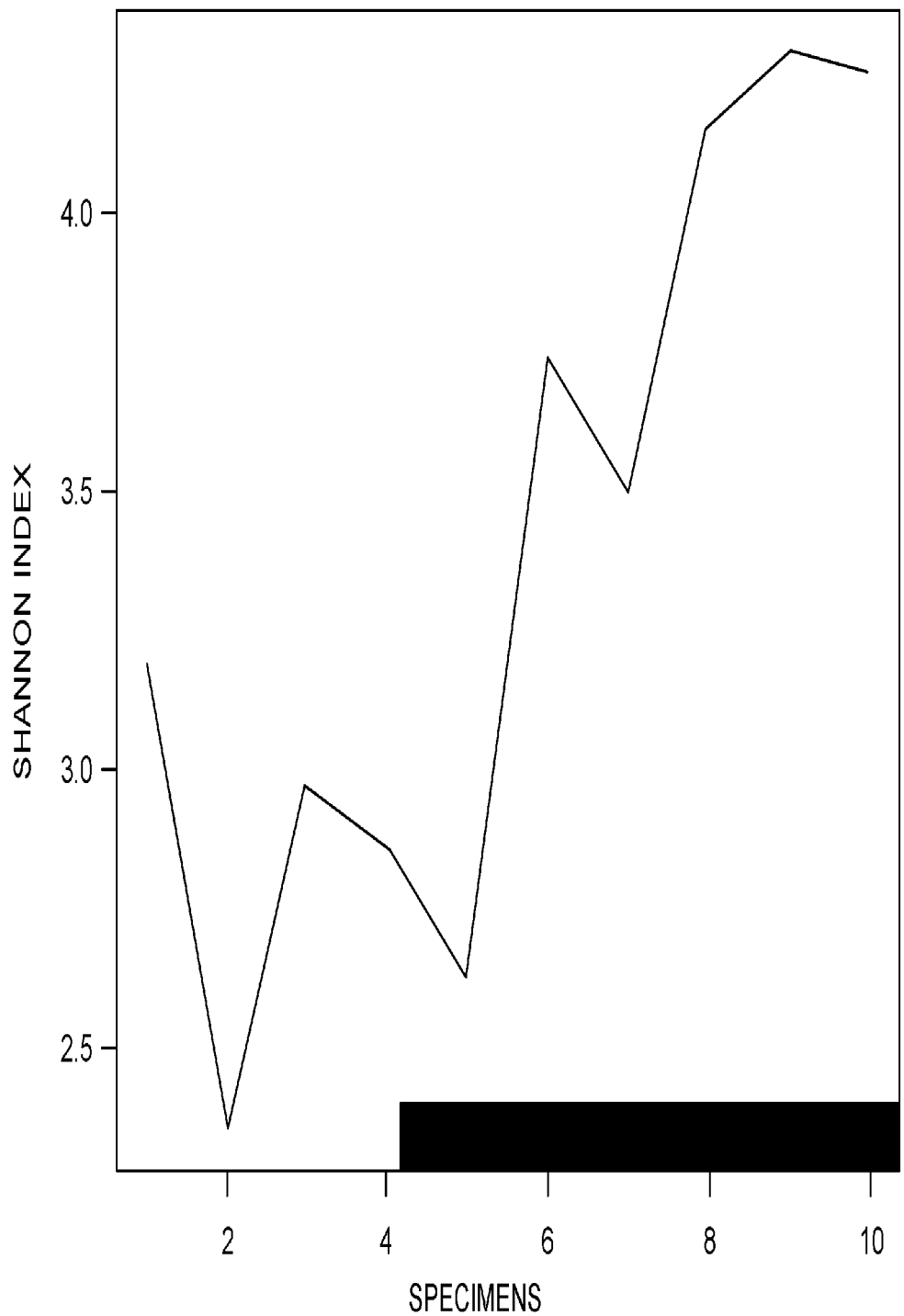
FIG. 8 depicts an aspect of ascertaining statistical significance of treatment epoch-related effect on microbiota diversity between the sampled epochs based on a distance-based multivariate analysis of variance (MANOVA) on microbiota diversity time series in relation to treatment metadata as a grouping variable, in accordance with an embodiment of the disclosure.

At step 230, an alpha or UniFrac diversity time series is determined. In one embodiment, a generalized phylogenetic-distance UniFrac diversity is calculated for each time series member. The UniFrac diversity may be variance-adjusted. In one embodiment, the alpha diversity (for example, Shannon, Simpson, or Chao) may be determined for each time series member. Some embodiments of step 230 may also utilize computation services 126, which may include the R-system gunifrac package, such as shown in the example computer program routine of FIG. 9A-9E. An additional example of computer program routine for performing aspects of steps 220, 225, and 230 is illustratively depicted in FIG. 10A for microbiota *F. prausnitzii*. In particular, the program routine of FIG. 10A determines UniFrac diversity (step 230) and uses a threshold of 5 in 10,000 or 0.05% (from step 215). With reference to FIG. 8, an example graphical depiction of a diversity time series is provided for an embodiment actually reduced to practice that corresponds to the computer code shown in FIG. 10A.

At step 235, from the determinations of the previous steps, a condition-related taxa abundance time series may be determined. The diversity and rarefacted abundance time series may be stored, at step 240 in an operational data store 207, such as storage 121 (FIG. 1A).

At step 245, an association of diversity with treatment-epoch is determined to ascertain the statistical significance of treatment epoch-related effect on microbiota diversity between the sampled epochs. In some embodiments, a distance-based multivariate analysis of variance (MANOVA) may be performed on diversity time series in relation to the treatment metadata, as a grouping variable. An example of computer program routine for performing aspects of step 245 is illustratively depicted in FIG. 10B for an embodiment actually reduced to practice. In this example embodiment, where the p value is determined to be less than 0.1, then it is determine that a significant difference is present.

At step 250, one or more time-series trend metrics may be determined to ascertain a statistical significance of time-related effects on the condition-related taxon or taxa. In some embodiments, an abundance time series trend analysis is performed on the one or more condition-related taxa pertinent to the subject's health condition. For example, in an embodiment, step 250 is carried out by utilizing Bayesian Hurst-Kolmogorov stochastic process methods (such as including H estimate or Mann-Kendall test). An example of computer program routine for performing aspects of step 250 is illustratively depicted in FIG. 10C for an embodiment actually reduced to practice for microbiota *F. prausnitzii*. In this example embodiment, where the p value is determined to be less than 0.05, then it is determine that a significant trend exists. The resulting MANOVA and trend analysis results may be stored and made accessible for subsequent reporting or retrieval.

As shown in the computer program code of FIG. 10C, a determination of joint significance (as described above) of microbiota diversity change statistical significance and taxa abundance change statistical significance is next performed. In this way, data from the determinations of steps 245 and 250 may be combined to synthesize an interpretation as to the presence of statistically significant microbiota change relevant to the health condition of interest. In one embodiment, a Boolean conjunction is performed of a Hurst-Kolmogorov H estimate >0.75 and MANOVA F-test p-value <0.05 and Bayesian Mann-Kendall p-value <0.05, which may use used to determine microbiota change meriting decision-making with regard to therapy effectiveness or disease exacerbation or remission or progression. The current determination of joint significance of microbiota diversity change statistical significance and taxa abundance change statistical significance also may be stored for comparison or use in future analyses, as additional specimens are collected and analyzed.

At step 275, where both determinations in steps 245 and 250 are determined to be significant (joint significance is determined), then method 200 proceeds to step 280, where a decision support tool running method 200 may initiate an intervening action, as described herein. For instance, a notification may be provided to a caregiver that a significant change has occurred in the subject, and/or another intervening action may be invoked or otherwise carried out. For instance, one intervening action comprises generating a notification that may be emitted or otherwise communicated to the patient or to a caregiver, such as a provider clinician responsible for the care of the patient. For example, an electronic advisory or warning message may be emitted to a human user, such as a caregiver, indicating a significant change in microbiota-related levels, which may indicate a change (or possible future change) in the patient's condition or that the current treatment is impacting the microbiota in a manner that may merit intervening treatment. In an embodiment, the action comprises generating and emitting or communicating the notification, which may be emitted/communicated via a bedside or patient-side alarm, user/clinician interface (such as interface 142 described in FIG. 1A), or may be communicated to a smartphone or personal computing device of a caregiver, thereby alerting them of a possible change to the patient's condition.

Another intervening action that may be initiated, based on the determined likelihood, comprises modifying a care plan or treatment procedure or a recommendation for modifying a care plan or treatment procedure associated with the patient; for example, automatically scheduling an appointment with a specialist or other healthcare resources for the patient, operating on the patient, or administering another similarly effective therapeutic intervention, such as changing the patient's treatment or diet. The recommendation may be provided in conjunction with a notification, and/or may be provided via a user/clinician interface, such as interface 142, described in connection with FIG. 1A.

Yet another action that may be initiated, based on the determined likelihood, comprises automatically modifying computer code executed in a healthcare software program for treating the patient, thereby transforming the program at runtime. For example in one embodiment, the modification comprises modifying (or generating new) computer instructions to be executed at runtime in the program, the modification may correspond to a change in a care plan, treatment procedure, or therapeutic intervention to be administered to the patient due to the determined joint significance. In one instance, the modification comprises changing the executed computer instructions corresponding to monitoring the patient's condition, such as increasing the frequency of obtaining physiological measurements of the patient, or increasing sensitivity of monitoring physiological changes in a patient.

Yet another action that may be initiated, based on the determined likelihood, comprises scheduling healthcare resources for the patient. For example in one embodiment, a physical therapy resource may be automatically reserved for the patient, healthcare staff may be notified and/or automatically scheduled, or transportation/support staff or resources for getting the patient to a healthcare facility may be called. In one embodiment, this action comprises modifying or updating a resource/scheduling electronic record in a resource/scheduling system, such as operated as part of a hospital or healthcare system. In one embodiment, the action comprises, upon a determined significance of microbiota-related change or trend, initiating a computer instruction that modifies the scheduling healthcare resources, which may include computer instructions for automatically alerting, scheduling, and/or notifying staff, reserving rooms, transportation, or other equipment/space, and which may include changing the priority of the patient (when compared to other patients) for receiving these resources.

Otherwise, according to the embodiment shown in FIG. 2, where either determination in steps 245 or 250 is determined to be not statistically significant (joint significance is not determined), then method 200 proceeds to step 290. In some embodiments, or step 290 method 200 may log a data entry (or emit a notification) indicating that the comparative non-superiority and non-inferiority of the two or more time periods and their respective treatment regimens can be emitted. Alternatively, some embodiments of step 290 do not emit a notification, and instead may wait until method 200 repeats for a future time period using next or subsequently specimen information. As described previously, an aspect of a decision support tool, comprising a computer program routine and implementing an embodiment of method 200 is illustratively provided in FIGS. 9A-9E and 10A-10C.

Example Reduction to Practice

An illustrative example embodiment of the present disclosure that has been actually reduced to practice is described herein. This example embodiment comprises a decision support tool which utilizes an improved smart sensor to detect statistically meaningful changes and trends in microbiota-related activity of the patient, as described herein, and upon such detection, initiates an appropriate intervening action. However, it should be noted that although this example reduction-to-practice focuses specifically on a specimen type or anatomical site (e.g., intestinal [fecal] microbiota) and on a health condition (Crohn's disease), embodiments of the technologies described herein are more generally applicable to serial microbiota measurements from any of a variety of anatomical sites or specimen types and any of a variety of health conditions.

With reference to FIGS. 1A, 9A-9E, 10A-10C, and with continuing reference to method 200 of FIG. 2, this example embodiment was constructed, tested, and verified as described below. Informed consent was first performed in 2 healthy control subjects and in 2 subjects with symptomatic Crohn's Disease (one with multi-year history under treatment; one newly-diagnosed and commencing treatment). Stool samples were collected at 48-hour intervals from subjects with a sterile cotton swab, dispersed into a vial containing preservative, stored at refrigerator temperature until shipping, and shipped by surface mail to the laboratory for processing.

Upon receipt of specimens at the performing laboratory, Epicentre ExtractMaster™ fecal DNA extraction kits were used to extract nucleotides from the specimens. Approximately 700 ng of DNA were extracted from each sample. Group, genus, and species-specific 16S rRNA determinations were performed. Bacterial rRNA sequencing was performed on the Illumina MiSeq™ platform or the Illumina NextSeq500™ platform. A 300-cycle 2×150 bp read configuration was utilized, yielding outputfiles of approximately 1.2 GB each. Output files were processed with Illumina BaseSpace™ software. Alternatively, MiSeg™ or NextSeg™ output files were processed with bcl2fastq software. To reduce the quantitative error of the detected bacteria OTUs and to characterize the changes in bacterial copies, the abundance of 16S rRNA gene copies was calculated from standard curves, and specific bacterial taxons were expressed as a percentage of the total bacteria determined by the universal primers.

As described in the description of method 200, samples with more than 10,000 reads were rarified to 10,000 reads, and taxa having abundance less than 0.05% were censored. Phylogenetic trees and alpha diversity metrics were calculated using the phyloseq package in Bioconductor (R system). Rarefaction and Alpha diversity measures were determined using the vegan package in R, and PD generalized UniFrac diversity calculations were performed using the GUniFrac package in R. PD-based multivariate analysis of variance (MANOVA) and F-test p-value significance was determined in relationship to time-series metadata denoting IBD treatment exposures by date. Bayesian Hurst-Kolmogorov H and Mann-Kendall tests and their significance levels for trend were determined on taxa abundance time series using the HKprocess package in R.

In this example embodiment, a computer system 120 running the Linux operating system (129) was utilized with the open-source software package R, and the R packages (computation services 126): GUniFrac package, as described above, and the HKprocess for utilizing the Hurst-Kolmogorov processes. This example embodiment also used the example computer program routine provided in FIGS. 9A-9E.

As used herein and in connection with the claims listed hereinafter, the terminology "any of clauses" or similar variations of the terminology is intended to be interpreted such that features of claims/clauses may be combined in any combination. For example, an exemplary clause 4 may indicate the method/apparatus of any of clauses 1 through 3, which is intended to be interpreted such that features of clause 1 and clause 4 may be combined, elements of clause 2 and clause 4 may be combined, elements of clause 3 and 4 may be combined, elements of clauses 1, 2, and 4 may be combined, elements of clauses 2, 3, and 4 may be combined, elements of clauses 1, 2, 3, and 4 may be combined, and/or other variations. Further, the terminology "any of clauses" or similar variations of said terminology is intended to include "any one of clauses" or other variations of such terminology, as indicated by some of the examples provided above.

Clause 1. A computerized decision support tool for facilitating diagnosis and treatment of a patient by detecting clinically meaningful activity in microbiota in the patient, comprising: a processor; computer memory having instructions stored thereon that when executed by the processor perform operations comprising: from a series of specimens acquired from the patient, determining a time series of measurements of microbiota abundances or taxa; receiving patient metadata associated with the measurements of the time series; performing rarefaction on each measurement's taxa abundances and normalizing taxon counts to a standard count; determining a microbiota diversity value for each measurement in the time series, thereby forming a diversity time series; determining a multivariate analysis of variance (MANOVA) on the diversity time series; determining a statistical trend analysis on the rarefacted abundance time series; based on a determined statistical significance of the MONOVA and the trend analysis, determining that clinically meaningful microbiota activity is occurring in the patent, and causing an intervening action regarding the human patient to be initiated.

Clause 2. The system of clause 1, wherein the intervening action comprises at least one of: issuing a notification to a caregiver associated with the patient; automatically scheduling healthcare resources for treating the patient; or modifying a computer program associated with a care plan for the patient.

Clause 3. The system of clauses 1 or 2, further comprising determining that the quality of the measurements of microbial taxa is adequate by performing a rank-abundance distribution fitting by least-squares.

Clause 4. The system of any of clauses 1-3, further comprising assembling a phylogenetic tree matrix with distance metric for the taxa represented in the time series.

Clause 5. The system of clause 4, wherein a Kimura 2-parameter (K80) model is utilized and the phylogenetic tree matrix is determined by Unweighted Pair Group Method with Arithmetic Mean (UPGMA) methods on the K80 distance matrix, for the taxa represented in the time series.

Clause 6. The system of any of clauses 1-5, further comprising filtering the taxa to retain genera-level taxa having abundance greater than a threshold.

Clause 7. The system of clause 6, wherein the threshold is 0.05%.

Clause 8. The system of any of clauses 1-7, wherein the microbiota diversity determination comprises abundance-weighted phylogenetic diversity (PD).

Clause 9. The system of any of clauses 1-8, wherein the trend analysis is performed utilizing a Bayesian Hurst-Kolmogorov stochastic process.

Clause 10. The system of any of clauses 1-9, wherein the specimens are acquired from an anatomical site (such as genitals or skin or pharynx) or specimen type (such as feces or blood or sputum) of the patient.

Clause 11. The system of any of clauses 1-10, wherein the series of specimens is determined from serial samples form the patient.

Clause 12. The system of any of clauses 1-11, wherein the series of measurements is determined utilizing 16S rRNA sequencing.

Clause 13. The system of any of clauses 1-12, wherein each measurement in the time series is received at an inter-sampling interval equal or greater than the cell-cycle generation time of the microbiota in log-phase growth.

Clause 14. The system of any of clauses 1-13, wherein the time series comprises measurements from at least 8 serial collected specimens.

Clause 15. A diagnostic method for detecting clinically meaningful activity in microbiota in the patient, the activity comprising a change or trend, the method comprising: acquiring at least 8 serial specimens from a subject, wherein at least 4 of the 8 specimens are from each of at least two treatment time periods or epochs that are to be compared; from the specimens, determining a measurement of abundances of microbial taxa thereby forming a time series; receiving treatment metadata for a health condition of interest, the treatment metadata associated with the time series; performing a statistical rank-abundance distribution fitting by least-squares to ascertain that the quality of the measurements of microbial taxa is adequate for subsequent analysis; assembling a phylogenetic tree matrix with distance metric for the taxa represented in the time series; performing rarefaction on each sample's taxa abundances, normalizing taxon counts to a standard count; calculating microbiota diversity each member of the specimen series; determining a multivariate analysis of variance (MANOVA) on the diversity time series in relation to treatment metadata as a grouping variable; performing a statistical trend analysis on the rarefacted abundance time series of one or more taxa related to the health condition of interest; based on the MANOVA and trend analysis, determining a significance of treatment epoch-related effect on microbiota diversity between sampled epochs thereby indicating clinically meaningful activity in microbiota of the subject.

Clause 16. The method of clause 15, wherein determining a measurement of abundances of microbial taxa comprises applying a 16S rRNA sequencing method including amplification, depending on the total count of organisms in the specimens and the efficiency of nucleotide extraction, and the resulting taxa abundance and metadata are stored in machine-readable persistent storage.

Clause 17. The method of clause 15 or 16, wherein the specimens are from an anatomical site (such as genitals or skin or pharynx) or of a particular type of specimen (such as feces or blood or sputum).

Clause 18. The method of any of clauses 15-17, wherein determination of operational taxonomic units (OTUs) in each specimen is performed by pyrosequencing of 16S microbial rRNA.

Clause 19. The method of clause 18, wherein the determinations of OTUs in serial specimens are repeated and periodic, sampling of a site or specimen type in a subject, such that the period of sampling is a longer time interval than is required for evolution of the microbiome in the site, under the conditions that are pertinent to the intended diagnostic or therapeutic purpose.

Clause 20. The method of clause 19, wherein a minimum sampling time-period for serial specimen collection (inter-sampling interval) is not shorter than the cell-cycle generation time of microbiota in log-phase growth (8 to 12 hours) and is at least several times a typical generation time or greater in length than three-fold multiple of cell-cycle times for the predominating OTUs, or 36 hours, whichever is greater.

Clause 21. The method of clause 20, wherein for excreta, the inter-sampling interval is not shorter than the usual residence time of a bolus passing through the length of the viscus, which for gut specimens is approximately 24 hours.

Clause 22. The method of any of clauses 15-21, wherein singleton OTUs that are detected in only one of the serial specimens have been discarded.

Clause 23. The method of any of clauses 15-22, wherein the measured taxa are filtered, retaining only genera-level taxa for subsequent steps.

Clause 24. The method of any of clauses 15-23, wherein only taxa having abundance greater than a threshold value of 0.05% of the total microbial count, are retained for subsequent steps.

Clause 25. The method of any of clauses 15-24, wherein the series of specimens is associated with a diagnostic health condition of interest in the subject sampled, with one or more taxa pertinent to management of the health condition, and with the subject's treatment metadata corresponding to the collection date on which each specimen was acquired.

Clause 26. The method of any of clauses 15-25, wherein rank-abundance distribution fitting by least-squares is performed preferably by fitting to a log-normal or Zipf-Mandelbrot distribution and the quality of the fit is determined by Q-Q, $R^2$ correlation coefficient, or other appropriate goodness-of-fit statistical metrics.

Clause 27. The method of any of clauses 15-26, wherein a phylogenetic tree matrix with distance metric is determined so as to enable determination of phylogenetic-distance-based diversity metrics, where the tree matrix is calculated via Unweighted Pair Group Method with Arithmetic Mean analysis of the K80 distance matrix.

Clause 28. The method of any of clauses 15-27, wherein the value of the standard microbial count for rarefaction is preferably 10,000 in the case of fecal microbiota time series.

Clause 29. The method of any of clauses 15-28, wherein the microbiota diversity is a numerical alpha diversity (for example, Shannon, Simpson, or Chao) or a generalized phylogenetic-distance UniFrac diversity.

Clause 30. The method of any of clauses 15-29, wherein the multivariate analysis of variance as a function of treatment epoch grouping is preferably a permutation- and distance-based MANOVA with associated F-test of statistical significance.

Clause 31. The method of any of clauses 15-30, wherein abundance time series trend analysis is performed on the one or more condition-related taxa pertinent to the subject's health condition by means widely known in the art (such as linear regression ANCOVA, Lanzante's test, Pettitt's test, Buishand's range test, Buishand's U-test, Standard normal homogeneity test, Wallis-Moore phase-frequency test, Bartels' rank von Neumann's ratio test, the Wald-Wolfowitz test, or the two-sample robust rank-order distributional test), or preferably by Bayesian Hurst-Kolmogorov stochastic process methods (including H estimate or Mann-Kendall test), to ascertain the statistical significance of time-related effects on the condition-related taxon or taxa.

Clause 32. The method of clause 31, wherein the one or more condition-related taxa pertinent to the subject's health condition is determined based on utilizing linear regression ANCOVA, Lanzante's test, Pettitt's test, Buishand's range test, Buishand's U-test, Standard normal homogeneity test, Wallis-Moore phase-frequency test, Bartels' rank von Neumann's ratio test, Wald-Wolfowitz test, or two-sample robust rank-order distributional test.

Clause 33. The method of clause 31, wherein the one or more condition-related taxa pertinent to the subject's health condition is determined utilizing Bayesian Hurst-Kolmogorov stochastic process.

Clause 34. The method of clause 33, wherein the Bayesian Hurst-Kolmogorov stochastic process includes an H estimate or Mann-Kendall test.

Clause 35. The method of any of clauses 31-34, wherein the resulting MANOVA and trend analysis results are stored in persistent machine-readable storage for subsequent reporting and retrieval.

Clause 36. The method of any of clauses 31-35, wherein the MANOVA and trend analysis results are combined to synthesize an interpretation as to the presence of statistically significant microbiota changes relevant to the health condition of interest.

Clause 37. The method of clause 36, wherein the combining comprises a Boolean conjunction of a Hurst-Kolmogorov H estimate >0.75 and MANOVA F-test p-value <0.05 and Bayesian Mann-Kendall p-value <0.05 denotes microbiota change meriting decision-making with regard to therapy effectiveness or longitudinal disease exacerbation or remission or progression during the time interval encompassed by the specimen time series.

Clause 38. The method of clause 37, wherein the current determination of the joint significance of microbiota diversity change statistical significance and taxa abundance change statistical significance is stored.

Clause 39. The method of clause 38, wherein an advisory interpretive message regarding the joint significance of the changes, if any, is electronically emitted to a caregiver associated with the subject.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. A computerized decision support tool for facilitating diagnosis and treatment of a patient by detecting clinically meaningful activity in microbiota in the patient, comprising:

a processor;
computer memory having instructions stored thereon that when executed by the processor perform operations comprising:
from a series of specimens acquired from the patient, determining a time series of measurements of microbiota abundances or taxa;
receiving patient metadata associated with the measurements of the time series;
performing rarefaction on each measurement's taxa abundances and normalizing taxon counts to a standard count;
determining a microbiota diversity value for each measurement in the time series, thereby forming a diversity time series;
determining a multivariate analysis of variance (MANOVA) on the diversity time series;
determining a statistical trend analysis on the rarefacted abundance time series;
based on a determined statistical significance of the MONOVA and the trend analysis, determining that clinically meaningful microbiota activity is occurring in the patent, and
causing an intervening action regarding the human patient to be initiated.

2. The system of claim 1, wherein the intervening action comprises at least one of: issuing a notification to a caregiver associated with the patient; automatically scheduling healthcare resources for treating the patient; or modifying a computer program associated with a care plan for the patient.

3. The system of claim 1, further comprising determining that the quality of the measurements of microbial taxa is adequate by performing a rank-abundance distribution fitting by least-squares.

4. The system of claim 1, further comprising assembling a phylogenetic tree matrix with distance metric for the taxa represented in the time series.

5. The system of claim 4, wherein a Kimura 2-parameter (K80) model is utilized and the phylogenetic tree matrix is determined by Unweighted Pair Group Method with Arithmetic Mean (UPGMA) methods on the K80 distance matrix, for the taxa represented in the time series.

6. The system of claim 1, further comprising filtering the taxa to retain genera-level taxa having abundance greater than a threshold.

7. The system of claim 1, wherein the microbiota diversity determination comprises abundance-weighted phylogenetic diversity (PD).

8. The system of claim 1, wherein the trend analysis is performed utilizing a Bayesian Hurst-Kolmogorov stochastic process.

9. The system of claim 1, wherein the series of measurements is determined utilizing 16S rRNA sequencing.

10. The system of claim 1, wherein each measurement in the time series is received at an inter-sampling interval equal or greater than the cell-cycle generation time of the microbiota in log-phase growth.

11. A diagnostic method for detecting clinically meaningful activity in microbiota in the patient, the activity comprising a change or trend, the method comprising:
acquiring at least 8 serial specimens from a subject, wherein at least 4 of the 8 specimens are from each of at least two treatment time periods or epochs that are to be compared;

from the specimens, determining a measurement of abundances of microbial taxa thereby forming a time series;

receiving treatment metadata for a health condition of interest, the treatment metadata associated with the time series;

performing a statistical rank-abundance distribution fitting by least-squares to ascertain that the quality of the measurements of microbial taxa is adequate for subsequent analysis;

assembling a phylogenetic tree matrix with distance metric for the taxa represented in the time series;

performing rarefaction on each sample's taxa abundances, normalizing taxon counts to a standard count;

calculating microbiota diversity each member of the specimen series;

determining a multivariate analysis of variance (MANOVA) on the diversity time series in relation to treatment metadata as a grouping variable;

performing a statistical trend analysis on the rarefacted abundance time series of one or more taxa related to the health condition of interest;

based on the MANOVA and trend analysis, determining a significance of treatment epoch-related effect on microbiota diversity between sampled epochs thereby indicating clinically meaningful activity in microbiota of the subject.

12. The method of claim 11, wherein determining a measurement of abundances of microbial taxa comprises applying a 16S rRNA sequencing method including amplification, depending on the total count of organisms in the specimens and the efficiency of nucleotide extraction, and the resulting taxa abundance and metadata are stored in machine-readable persistent storage.

13. The method of claim 11, wherein the specimens are from an anatomical site or of a particular type of specimen.

14. The method of claim 11, wherein determination of operational taxonomic units (OTUs) in each specimen is performed by pyrosequencing of 16S microbial rRNA.

15. The method of claim 14, wherein the determinations of OTUs in serial specimens are repeated and periodic, sampling of a site or specimen type in a subject, such that the period of sampling is a longer time interval than is required for evolution of the microbiome in the site, under the conditions that are pertinent to the intended diagnostic or therapeutic purpose.

16. The method of claim 15, wherein a minimum sampling time-period for serial specimen collection is not shorter than the cell-cycle generation time of microbiota in log-phase growth and is at least several times a typical generation time or greater in length than three-fold multiple of cell-cycle times for the predominating OTUs, or 36 hours, whichever is greater.

17. The method of claim 16, wherein for excreta, the inter-sampling interval is not shorter than the usual residence time of a bolus passing through the length of the viscus, which for gut specimens is approximately 24 hours.

18. The method of claim 11, wherein singleton OTUs that are detected in only one of the serial specimens have been discarded.

19. The method of claim 11, wherein rank-abundance distribution fitting by least-squares is performed preferably by fitting to a log-normal or Zipf-Mandelbrot distribution and the quality of the fit is determined by Q-Q, $R^2$ correlation coefficient, or other appropriate goodness-of-fit statistical metrics.

20. The method of claim 11, wherein a phylogenetic tree matrix with distance metric is determined so as to enable determination of phylogenetic-distance-based diversity metrics, where the tree matrix is calculated preferably by UPGMA methods on the K80 distance matrix.

* * * * *